United States Patent [19]
Colby et al.

[11] Patent Number: 4,944,921
[45] Date of Patent: Jul. 31, 1990

[54] AUTOMATED PCB ANALYZER SYSTEM

[75] Inventors: Bruce N. Colby, Carlsbad; Eugene A. Burns, Solana Beach, both of Calif.

[73] Assignee: Maxwell Laboratories, San Diego, Calif.

[21] Appl. No.: 586,665

[22] Filed: Mar. 6, 1984

[51] Int. Cl.$^5$ .................. G01N 27/62; G01N 30/70; G01N 30/86

[52] U.S. Cl. .................. 422/70; 436/126; 436/161; 436/175; 422/82.02

[58] Field of Search ............ 422/61, 68, 69, 90; 436/104, 126, 161, 175, 178

[56] References Cited

U.S. PATENT DOCUMENTS

| | | |
|---|---|---|
| 1,775,134 | 5/1929 | Malsbury . |
| 3,286,177 | 10/1962 | Boer et al. .................. 324/103 |
| 3,365,931 | 7/1964 | Mac Ritchie et al. .......... 73/23.1 |
| 3,404,260 | 10/1968 | Johnson, Jr. .............. 73/23.1 X |
| 3,518,059 | 5/1967 | Levy .......................... 23/232 |
| 3,528,775 | 1/1967 | O'Hara et al. ................ 23/230 |
| 3,544,275 | 6/1967 | Habermas et al. ............. 23/230 |
| 3,555,260 | 1/1971 | Karohl .................... 73/23.1 X |
| 3,653,839 | 7/1970 | Luks et al. ................... 23/230 |
| 3,715,189 | 2/1973 | Nighossian et al. ............ 23/259 |
| 3,860,393 | 2/1972 | Campen, Jr. ................. 23/230 |
| 3,898,837 | 9/1973 | Boege ........................ 73/23.1 |
| 3,944,389 | 3/1974 | Solomon . |
| 4,002,052 | 4/1975 | Bordet et al. ................ 73/23.1 |
| 4,003,257 | 3/1975 | Fletcher et al. .............. 73/23.1 |
| 4,028,060 | 3/1975 | Godsey ....................... 23/293 |
| 4,042,326 | 9/1975 | Kallos ........................ 23/230 |
| 4,077,773 | 3/1978 | Stearns . |
| 4,101,278 | 7/1978 | Hartmann . |
| 4,166,379 | 9/1978 | Bradshaw .................. 422/88 X |
| 4,203,725 | 2/1978 | Snowden, Jr. et al. .......... 23/230 |
| 4,229,868 | 9/1978 | Muldoon ..................... 73/23.1 |
| 4,235,839 | 12/1978 | Vesterberg .................... 422/58 |
| 4,236,404 | 8/1976 | Ketchum et al. ............... 73/19 |
| 4,238,197 | 4/1979 | Eisentraut et al. ............. 23/230 |
| 4,266,277 | 4/1979 | Issenmann ................... 364/498 |
| 4,288,402 | 4/1979 | Ellis ............................ 422/61 |
| 4,305,276 | 12/1981 | Mueller ..................... 73/23.1 |
| 4,307,453 | 6/1979 | Kleiss ....................... 364/833 |
| 4,338,811 | 7/1982 | Miyagi et al. ............... 73/23.1 |

OTHER PUBLICATIONS

Takeshita et al., Chemical Abstracts, vol. 88, 1978, No. 88:141375e.
Albro et al., J. Chromatog., vol. 205 (1981), 103–111.
Tuinstra et al., J. Chromatog., vol. 204 (1981), 413–419.
Tindall et al., J. Chromatog., vol. 196 (1980), 109–119.

*Primary Examiner*—Robert J. Hill
*Attorney, Agent, or Firm*—Fitch, Even, Tabin & Flannery

[57] ABSTRACT

Method and apparatus for the detection and quantitation of polychlorinated biphenyls (PCB's) utilizing sample preparation by treatment with predetermined quantities of sulfuric acid and lower alkane, in which the alkane—extracted phase is subjected to chromatographic separation of PCB components (116) and electron capture detection of the separated PCB components (118), and in which the detector response is analyzed by pattern recognition comparison (316) for determination and quantitation of PCB's presented in the sample with stored data for standard PCB mixtures.

5 Claims, 3 Drawing Sheets

AUTOMATED PCB ANALYZER SYSTEM

This is a continuation-in-part of International Application No. PCT/U.S.83/00325, filed Mar. 7, 1983 under the provisions of the Patent Cooperation Treaty and designating the United States.

BACKGROUND OF THE INVENTION

The present invention is directed to systems for detection and analysis of halogenated aromatic hydrocarbons, and more particularly to automated gas chromatographic analysis systems for detection and quantitation of polychlorinated biphenyls.

Polychlorinated biphenyls (PCB's) have been manufactured and used in large quantity for use as dielectric materials for electrical equipment such as transformers and capacitors. Polychlorinated biphenyls have been conventionally manufactured by chlorinating biphenyl and have been sold as products having a predetermined, desired degree of chlorine substitution of the reaction mixture, generally having a distinctive distribution of PCB compounds and isomers characteristic of the particular PCB product. For example, polychlorinated biphenyl compositions having respectively, 41, 42, 54 and 60 weight percent of chlorine have been commercially marketed, each having a different characteristic mixture and proportion of PCB compounds and isomers.

Unfortunately, it has now been recognized that such materials pose a significant health threat which has been widely dispersed. Accordingly, methods and apparatus which may be utilized in the field for on site detection and quantitation of such materials would be desirable. Conventional analysis of PCB's in environmental samples is carried out by extraction of PCB compounds from the environmental sample (oil, sludge, soil, etc.) by means of an organic solvent, which is analyzed by gas chromatograph. However, conventional PCB extraction and gas chromatographic analysis procedures are time consuming and not well adapted for on site utilization by relatively unskilled personnel. Because of the wide spread distribution of PCB's, there is a need for field analysis systems for routine PCB analysis.

Accordingly, it is an object of the present invention to provide improved methods and apparatus for the detection and quantitation of polychlorobiphenyls. It is a further object to provide a rugged, portable instrument and PCB testing procedure which may be utilized by relatively untrained personnel in the field for analysis of PCB's. These and other objects of the invention will become more apparent from the following detailed description and the accompanying drawings, of which

BRIEF DESCRIPTION OF THE SOFTWARE

Figure 1:
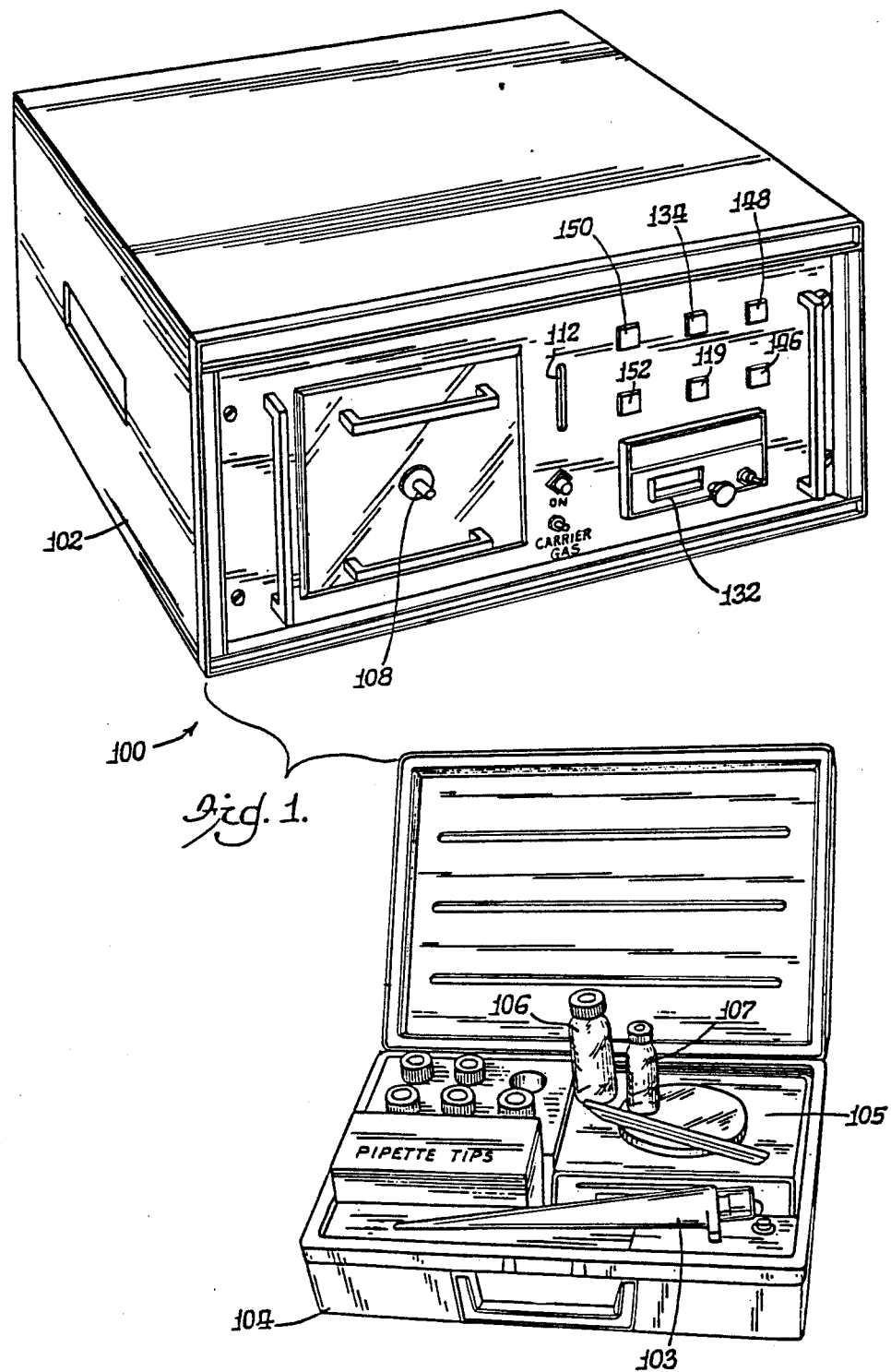
FIG. 1 is a perspective view of an embodiment of an automated field analyzer system for polychlorinated biphenyls in accordance with the present invention.

Following the description of the invention, a program is set forth, in assembly language, which could be part of the contents of a memory of a microprocessor included in the analyzer system of the present invention.

Also following the description of the invention, another program is set forth, in a higher level language, which could also be part of the contents of the memory of the microprocessor, for functioning as a driver for the assembly language program.

Generally in accordance with the present invention, methods and apparatus are provided for the detection and quantitation of polychlorinated biphenyls. In accordance with method aspects of the invention, a predetermined amount of sample to be tested is simultaneously mixed with predetermined quantities of concentrated sulfuric acid and a lower alkane such as hexane. Some samples such as soils may desirably first be extracted with a lower alcohol solvent such as methanol to provide a fluid sample for sulfuric acid/alkane processing. Subsequently, a predetermined sample portion of the hexane phase is subjected to gas chromatographic separation of PCB components and electron capture detection of the separated PCB components.

In accordance with apparatus aspects of the invention, a sample preparation kit is provided comprising means for measuring a predetermined sample quantity of sulfuric acid and lower alkane processing agents, which are preferably provided in premeasured quantities for individual sample treatment, and a container for mixing the measured sample and the processing agents. The analysis system further includes an automated gas chromatographic detector comprising a gas chromatographic column for separating polychlorobiphenyl components, an electron capture detector for detecting separated component peaks from the gas chromatographic column, and means for recording the peak elution times and detector response areas. The apparatus further includes means for storing standard peak elution times and detector response data for a plurality of standard PCB mixtures, means for comparing the sample data with the PCB standard data for recognition of a substantially similar elution pattern therewith and means for calculating the PCB sample concentration of a PCB sample having an elution pattern substantially similar to a stored standard PCB elution pattern. Detector response peak areas and peak elution times are calculated and stored, and subsequently compared with stored peak area and elution time data for a plurality of standard PCB mixtures each comprising a different blend of PCB components. A cosine theta pattern recognition algorithm is particularly preferred for comparison. Upon recognition of similarity with a PCB standard, the PCB concentration is calculated based on detector response, sensitivity and predetermined sample size.

As indicated, in accordance with the present invention, methods and apparatus are provided for the gas chromatographic/electron-capture detection determination of polychlorobiphenyl compounds in transformer oils, sludges, sediments and soils by a field-usable instrumental analysis method. Important features of the system are a sampling pretreatment kit to extract and isolate PCB's from sample substrates (e.g., oil, soil, sludge, etc., matrices), and electron-capture detector gas chromatograph apparatus having PCB pattern recognition capability for recognition of specific PCB isomer mixtures. In accordance with various aspects of the present disclosure, PCB determinations may be made in a short time (e.g., less than one hour) by field personnel and without the assistance of personnel skilled in analytical chemistry. In this regard, the extraction and cleanup time can be reduced by direct cleanup and extraction at the test site. For example, a predetermined quantity, such as a one-gram sample of the sample substrate (transformer oil, soil, etc.), can be transferred to a glass vial having a volume in the range of 40- to 50-ml. Predetermined amounts of concentrated sulfuric acid and a lower alkane partition solvent may be combined with the sample. The sulfuric acid/alkane processing agents may be conveniently stored, for example, in a quick-break stemmed ampoule, or a glass vial which may serve as the mixing chamber for the sample and processing agents. The components are mixed for a limited time period which may be less than ten minutes and desirably less than a minute. The concentrated sulfuric acid, which desirably is at least 95 percent by weight and preferably 98 percent by weight $H_2SO_4$, does not react with polychlorinated biphenyls, but does react with and retain a wide variety of potentially interfering materials. The PCB compounds themselves are preferentially partitioned into the alkane layer, which separates on the top of the mixture upon cessation of mixing. For simple samples, such as transformer oils, the sample treatment and preparation can be accomplished in a few minutes. For more complicated samples, including solid components, such as soils, sludges, etc., the sample is desirably first extracted with a lower alcohol, preferably methanol. In this regard, a predetermined amount (such as one gram) of the sample is mixed with a predetermined quantity of alcohol. After mixing, a predetermined amount of the alcohol phase is subsequently utilized as a fluid sample in the previously described alkane/sulfuric acid sample processing procedure.

Illustrated in FIG. 1 is an automated PCB analysis system 100 which includes a sample preparation kit 104 and a microprocessor controlled PCB analyzer 102. The sample preparation kit 104 includes pipet 103 and balance 105 for measuring predetermined quantities of fluid and solid samples, respectively. The kit further may include a plurality of glass vials 106 containing premeasured quantities of sulfuric acid (5 ml.) and hexane (5 ml.) for sample processing, and a septum-capped vial 107 containing a PCB standard for instrument calibration. Vials containing a premeasured amount of methanol may also be included in the kit 104.

After processing of the sample with the sulfuric acid/alkane mixture, a suitable sample portion of the upper organic (e.g., hexane) phase may be removed by a syringe from the vial 106 and injected into the heated sample inlet of the gas chromatograph detection apparatus 102.

The illustrated apparatus 102 (FIG. 1) comprises a conventional injection port 108, a printer 132, a carrier gas flow rate indicator and control 112 and a number of indicators and controls including a calibration control 148, an analysis-in-process indicator 134, a sample initiation control 150, a print temperature control 152, an over power indicator 119, and a power "on" control 146.

The portable PCB analyzer 102 illustrated in FIG. 1 is an automated instrument for identifying and measuring polychlorinated biphenyls such as commercial Aroclor mixtures 1260, 1254, 1242 and 1016 sold by Monsanto Chemical Company of St. Louis, Missouri. The PCB detection is carried out by utilizing an electron-capture detector equipped gas chromatograph, operated at an elevated temperature, with accompanying sample plumbing, data processing and output electronics. The instrument 102 is highly automated and field portable. PCB's are recognized using microprocessor controlled pattern recognition techniques, and quantitation is achieved automatically through comparison with known standards. The instrument 102 has in addition, limited ability to compensate for interferences, as will be discussed. PCB detection is accomplished at elevated temperatures with an electron-capture detector in series with a gas chromatographic column. Samples are introduced by syringe injection through a septum into the column by means of the injection port 108. A reference sample of known composition and concentration may be periodically injected into the apparatus 102 to provide periodic calibration and sensitivity checks.

The electron-capture detector utilizes the high electron affinity of compounds with halogen group elements to provide a measurable signal, and is accordingly particularly adapted for PCB determination. A sample is separated into components by means of a gas chromatographic column. For PCB determination, this column may comprise a conventional siloxane polymer (such as OV-101 siloxane polymer of Ohio Valley Company) coated on an inert solid support.

In the detector module, a scandium tritide ($Sc^3H_3$) foil provides a source of beta particles which ionize dry nitrogen carrier gas and develop a secondary electron flow, termed the standing current. The detector collects these electrons, and an electrometer measures the current. An electonegative material such as a PCB will capture electrons from this ionized gas stream. The presence of an electonegative compound flowing through the detector thus decreases the standing current (by absorbing electrons) in proportion to the concentration of the electron-capturing substance. The electrometer detects this change in current, and provides an output voltage proportional to the concentration of gas.

An important part of the automated PCB analysis instrument 102 is the utilization of microprocessor controlled pattern recognition logic. In this regard, the integrated current/time output of the detector, after injection of the sample is digitally stored by the instrument 102. This set of current/time output (integrated areas) varies for each of the potential PCB mixtures. By comparing the relative output integrated areas at the specific intervals of the gas chromatographic output, pattern recognition routines may be utilized, as subsequently described in more detail, to identify which PCB groups of compounds are present. By comparing the peak area response of the unknown sample with those of standards or calibration mixtures, the amount of each specific PCB can be calculated. By using a constant amount of sample substrate, (such as transformer oil, soil, sludge, etc.), the output may be provided in the units of mg PCB (Arocolor type) per kg sample (ppm).

If the pattern recognition routine cannot clearly discern the presence or absence of any of the common PCB mixtures, the instrument will signal the operator to request more detailed laboratory analysis of the sample, as will be more fully described.

The detector output signal is converted to a succession of digital values which are evaluated within the onboard dedicated microcomputer. This evaluation comprises converting the successive digital values to a series of peak area/retention time pairs. The relative magnitudes of the peak areas and their retention times are compared by the microcomputer to reference data in its memory to determine if specific PCB mixtures are present. If a specific PCB mixture (Aroclor) is identified, concentrations are calculated in the microcomputer by comparing the peak areas to stored reference data. These concentrations are statistically evaluated, statistically improbable peaks ("outliers") are rejected, and a final mean concentration reported at the printer.

The instrument 102 may be calibrated by means of one or more of a known set of PCB standards in hexane and verifying that the desired output is obtained. If the measured values do not correspond to the actual values for the measured standard, the instrument calibration factors are adjusted to compensate for the deviations. The unprocessed analog signal from the electrometer is available at a BNC connector on the rear panel. This output may be connected to a strip chart recorder set for, 0.5 volt full-scale. Processed data in the form of PCB percentage is provided by means of the paper tape printer on the front of the unit.

The PCB analyzer 102 may also contain suitable programs to plot acquired data on the printer during acquisition, advise the operator of problems encountered with the results and recommend possible solutions to those problems, request injection of calibration check and other quality control samples.

Figure 2:
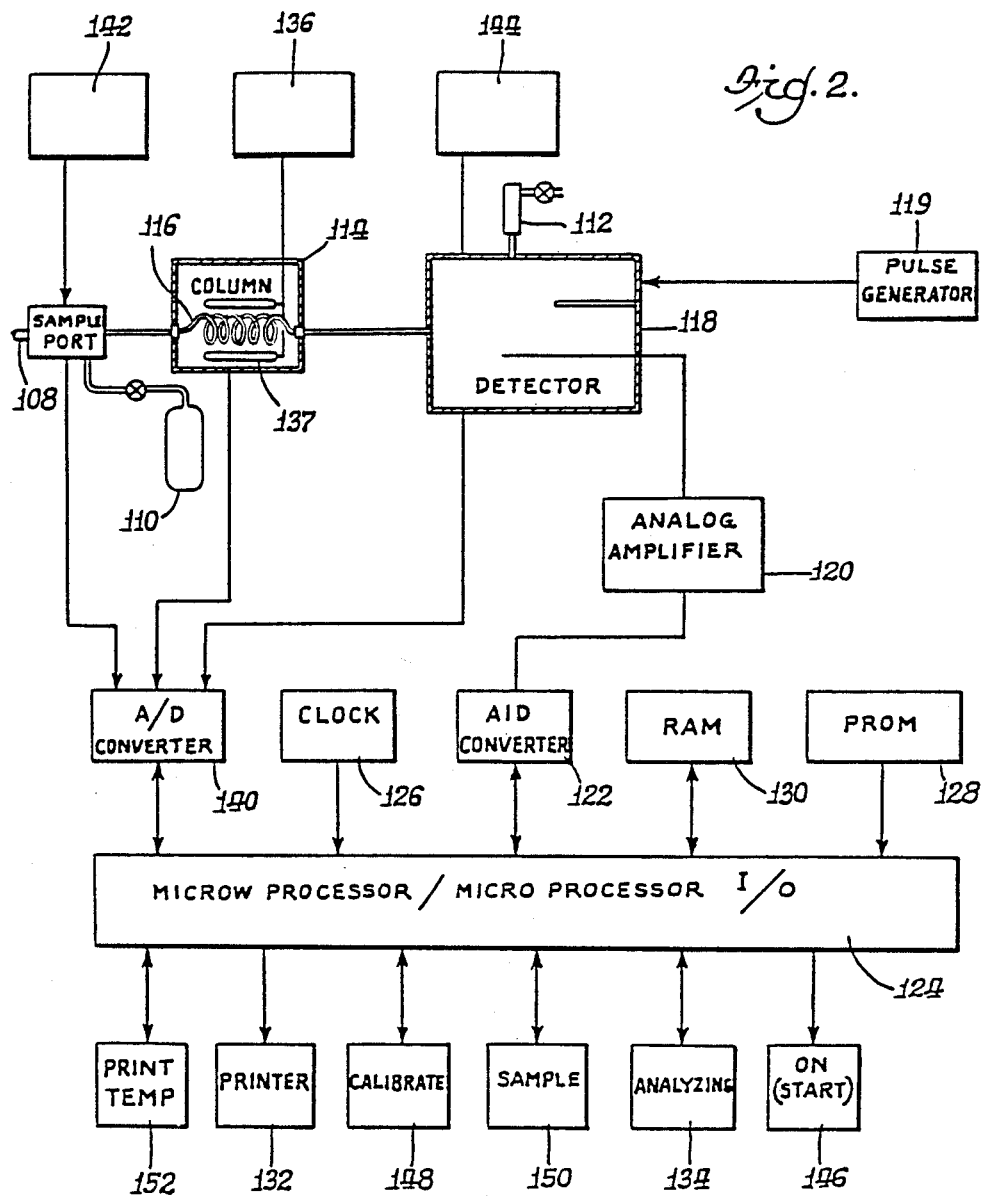
FIG. 2 is a block schematic diagram of various of the components of an embodiment of an automated PCB analyzer like that of FIG. 1.

Turning now to FIG. 2, various internal features of the device 102 will be further described. As illustrated in FIG. 2, the PCB analyzer 102 comprises a conventional heated sample injection port 108 having a nitrogen inlet port to which may be connected a high purity nitrogen supply 110. Carrier grade or oxygen free nitrogen ($N_2$) is connected to the instrument by means of a flexible tubing. Gas control hardware includes a fitting for an external gas supply on the rear panel of the instrument, a carrier gas flowmeter, metering valve, and interconnecting plumbing. During operation of the gas chromatograph, nitrogen carrier gas is passed through the column into the electron-capture detector, and then vented. Gas flow may be adjusted, by means of a suitable metering valve, to provide a flow of 25 ml/min, as indicated on the front panel meter. After opening the nitrogen valve, gas must be allowed to flush the lines, gas chromatographic column and detector.

The apparatus 102 further comprises a heated gas chromatographic column 116 located within a suitable insulating oven 114 containing electrical resistance heating elements 137 under control of heating circuit 136. The column output is directed to heated detector 118 which is supplied with pulse generator 119.

The gas chromatograph/detector assembly may be substantially similar to the commercially available electron-capture gas chromatographic apparatus such as that utilized in the Model 215ACA automated monitor of Systems, Science and Software (now S-Cubed) of San Diego, California, and as described in U.S. Pat. Nos. 4,112,302 and 4,156,813. The gas chromatographic apparatus should be provided with an isothermal oven for maintaining the gas chromatographic column at a desired elevated temperature (180°-200° C.). A scandium tritide ($ScH^3$) source is desirably used in the electron-capture detector (to meet applicable NRC regulations regarding transfer and sale of equipment without requiring a special license). The use of other electron-capture detector beta sources, however, is also contemplated. A heated inlet system sample valve is incorporated to facilitate injection of liquid samples, and a liquid/gas sample splitting system may be incorporated in the gas chromatograph to facilitate appropriate dilution, as will be more fully described.

The detector output is directed to high gain analog amplifier 120, the output of which is received as an input to the analog to digital converter 122. The analog to digital convertor receives the analog output from the amplifier 120 and periodically converts this output to a digital value which may be addressed as a digital input to microcomputer 124.

In this regard, the PCB Analyzer 102 incorporates a dedicated microcomputer 124 for analyzing the digitized sample data. The microcomputer is desirably a bus-oriented system such as the Motorola eight-bit 6809 microprocessor chip and associated input-output device circuitry for the microprocessor. The microcomputer system 124 as shown, includes the system I/O devices. A wide variety of peripheral data acquisition systems can be easily interfaced to the PCB analyzer by virtue of its bus-oriented architecture. The A/D converter and microcomputer and microcomputer I/O circuitry 124 operate under the timing control of clock 126. The microcomputer 124 has further data input from programmed read-only memory (PROM) 128, and has operating access to random access memory 130. The microcomputer has as an output device printer 132 and status lights 134 which indicates when a sample is being analyzed.

As indicated, the column is maintained at an elevated temperature by an appropriate analog circuit 136 (the output of which may be adjusted by a suitable trimmer resistor) and resistance elements 137 within the column oven. The circuit 136 is provided with an output light 119 which indicates when power is being provided to the column oven resistance elements. The output from thermocouple temperature sensing elements in the column is converted to a digital value by the analog to digital (A/D) converter 140, which further provides input to the microcomputer 124. Similarly, the sample injection port and detector are heated to appropriate temperatures by means of similar resistance heating element circuitry 142, 144, respectively. The respective temperature of the injection port and detector are similarly converted to digital values, by A/D converter 140 and provided in digital form to microcomputer 124. The microcomputer 124 may be directed by the operator to print out the temperature of the injection port, column and detector by "print temp" switch 152. Additional input status switches to the microcomputer are "on" switch 146, calibrate switch 148 and sample switch 150.

A sample to be tested is injected in a conventional manner through a septum into an injection port 108, into a flow of carrier gas, which in the illustrated embodiment 102 is high purity nitrogen. The carrier gas with the injected sample flows through column 116 at a predetermined velocity adjusted by valve and flowmeter. The PCB sample constituents are separated in the column so that they have different elution times. The column discharge flows to the electron capture detector 118 in which the various PCB compounds, if present, absorb the electrons passing between the detector electrodes and disposed within the detector and thereby reduces the electron flow. The decrease in the electron flow is measured and amplified by an analog amplifier circuit 120 which may be of conventional design.

In this regard, after passing through the column, the carrier gas and any accompanying sample flow to the detector, which includes an electrically conductive housing, a central electrode, and a source of ionizing electrons preferably a beta source such as ScH$^3$. The central electrode is encased within and is electrically separated from the electrically conductive housing. A vent for the gas in the housing is provided by a tube connected to the housing and the flow of gas through the system is monitored by a gas flow meter connected to the outlet of the tube. The housing is repeatedly pulsed to a negative voltage by the pulse generator 119. The ionizing source in the detector produces energetic electrons by means of radioactive decay. These energetic electrons in turn ionize any gas present between the conductive housing and the electrode producing less energetic secondary electrons. Repeated pulsing of the conductive housing drives the secondary electrons toward the electrode where they are collected and produce a current which is measured and amplified by an analog circuit. PCB components function as electron capture materials, particularly in view of their halogen content. Accordingly, any PCB elution peak passing through the detector absorbs and thereby reduces the electron flow or current in proportion to the concentration of the PCB component.

Figure 3:
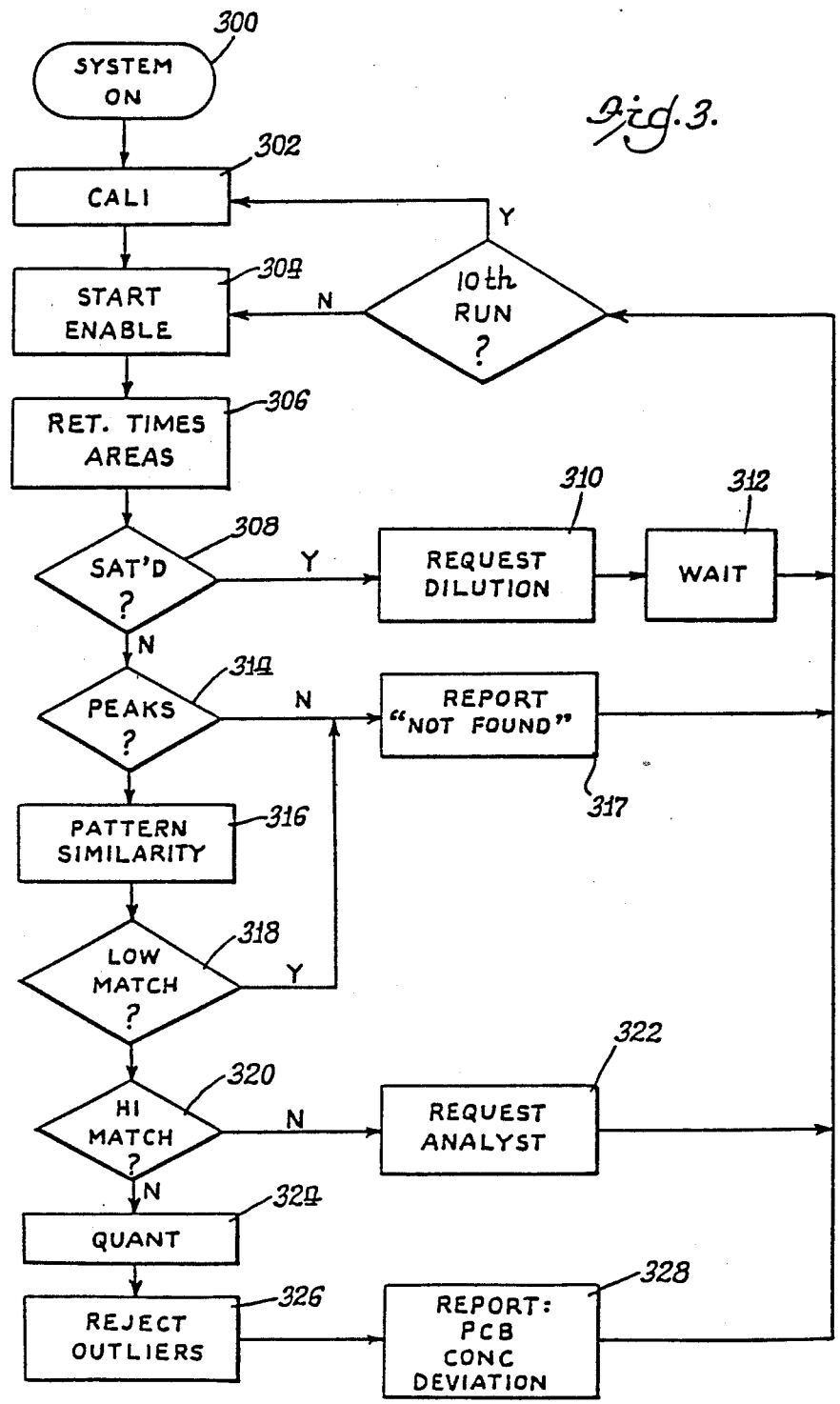
FIG. 3 is an embodiment of a logic flow diagram for the operation of an automated PCB analyzer like that of FIG. 1.

FIG. 3 illustrates a logic flow diagram for the PCB analyzer 102, from which appropriate software coding may be provided. The specific software coding will vary with the particular microprocessor system and associated hardware utilized.

As illustrated in FIG. 3, upon turning the system on the system waits to achieve the appropriate temperature equilibration conditions in the column, injection port and analyzer by means of calibration routine 302. To carry out a calibration, a predetermined sample size of a predetermined standard PCB mixture is injected into the instrument, and the respective elution peak areas and elution times for the calibration sample are stored in a calibration memory portion of RAM 130. The relative retention times and the peak areas are compared with stored values for the standard in PROM 128. If the calibration values are sufficiently similar to the stored "expected" values, then the instrument is considered to be operating properly and the appropriate calibration sensitivity factors for the instrument based on the known PCB concentrations in the sample are retained in RAM memory for sample quantitation purposes as will be more fully described. It should be noted that the hexane portion of the injected sample passes relatively rapidly through the column to the detector, where it is detected. Elution times are calculated from the time of the detection of the hexane carrier. Moreover, relative retention times for the peaks of the calibration sample are important for comparison with the calibration standard, and for this purpose, the elution times are compared by an appropriate normalizing factor which is the ratio of the elution time of the largest peak of the stored standard data to the elution time of the largest peak of the calibration sample.

Upon calibration, the operator may start the testing of an unknown sample by activating the start switch 150 on the PCB analyzer 102 (initiating the start enable module 304) and by injecting the sample. This initiates a sample run, pursuant to which the detector output is converted to digital values and the retention times and the areas of the respective peaks from the sample run are stored in memory 130 by means of routine 306. Upon completion of the run, the retention times and areas are checked against an overflow value by saturation routine 308 to determine whether the sample contained an excessive amount of PCB's to be analyzed. In this regard, the maximum sensitivity of the instrument analog output is nominally 10 volts, and a sample output value of 10 volts for any peak indicates a saturated condition. If the output is saturated, the PCB analyzer routine 310 requests that the operator dilute the sample, by printing out an appropriate message, and enforces a waiting period of up to 30 minutes or more to permit the column to be "flushed out" of the excessive PCB components, which were introduced during the preceeding run. The gas chromatograph inlet system may be modified to permit splitting of the sample by either 1 to 10 or 1 to 1000, and the diluted portion is transferred to the gas chromatographic column. Alternatively, the dilution step can be handled by transferring a small portion of the organic layer to a separate vial containing a known quantity of pesticide hexane; the diluted sample is mixed carefully and then a portion of the diluted sample is then injected into the gas chromatograph.

In the event that the output is not saturated by exceeding the maximum device output range, the retention time and area information stored for the preceeding run is checked for the existence of peaks by peak detection module 314. If the output is "flat" (i.e., no peaks), routine 317 directs the printer of the device 102 to report that there were no PCB's present in the sample.

In the event that there are peaks present in the stored peak retention time-area information for the sample run, routine 316 of the apparatus 102 determines pattern similarity of this stored sample data, with predetermined stored PCB patterns in the non-volatile memory of the apparatus 102. The pattern similarity algorithm 316 is a cosine theta pattern recognition algorithm utilizing multi-variant statistical analysis. Such pattern recognition algorithms are generally well known. In this regard, the stored peak retention time and peak area data for the unknown sample is represented as a vector in n-dimensional space, as are each of the stored retention time and area data sets for the respective stored PCB patterns. Each respective different peak of the sample (and stored standard data) is regarded as a separate dimension, with the integrated peak height-time area representing the position value of that dimension. The cosine theta pattern recognition algorithm 316 determines the difference in angle between the unknown sample vector in n-dimensional space and each of the respective PCB standard vectors. As previously indicated, it is relative elution times for the measured peaks which is important in the pattern recognition, and the peak elution time/area table for the sample is "normalized" for the comparison by a factor corresponding to a ratio of the elution time of the largest stored PCB standard peak and the largest sample peak (ratios with several sample peaks may be calculated successively to provide better pattern recognition). Two thresholds of difference of the sample vector angle from each of the PCB standard vectors are established, and stored in PROM. The first threshold represents substantial similarity or identity between the unknown sample vector and the particular PCB standard vector. The second threshold indicates a strong similarity which is strongly suggestive of the presence of PCB's, which requires further, more detailed analysis. If the difference in angle between the unknown vector, and the closest of the standard PCB vectors stored in nonvolatile memory is below the second threshold, then low match subroutine 318 directs the printer to report the absence of PCBs by module 317 as in the case of the absence of any output peaks from the unknown sample. If the cosine theta correlation between the sample of the n-dimensional unknown sample vector and the most similar standard PCB vector is between the first and second threshold values, but does not equal or exceed the high correlation value, high match subroutine 320 directs through request analysis subroutine 322 that the printer print a message to the operator advising the operator to request further laboratory analysis of the sample.

If the n-dimensional vector angle of the unknown sample has a high cosine theta match (i.e., close to one) with any of the stored standard PCB vectors, as previously discussed, then the quantitative amount of the PCB sample is determined by module 324, based on the current instrument sensitivity factors determined by the calibration run of the calibration standard. The area (peak height integrated over elution time) of each of the stored peaks is converted to a quantitative value, and a table of quantitative values is stored in the random access memory corresponding to each of the respective peaks stored for the unknown. Each peak may have a different sensitivity and a different calibration factor. For example, a first peak may have an area value of 10,000 arbitrary units which may be converted to a concentration of, say, 50 parts per million by application of the appropriate conversion factors and apparatus sensitivity based on the previous calibration run.

Following the quantitative determination of each of the unknown peaks, subroutine 326 determines the "reasonableness" of the quantitative values of each of the peaks, based on the particular PCB standard with which the unknown sample vector had the closest match. For example, if a particular calculated sample concentration calculated for a peak area deviates by, for example, more than two standard deviations from the mean of the concentration values calculated from all sample peaks, it may be presumed that this component peak may have suffered interference from some other non PCB component, or that other error may be involved. Subroutine 326 eliminates these "outlying" values from the unknown sample concentration tables which were generated by subroutine 324. Using the remaining values which have been determined to be reasonable values, the concentration of the particular PCB is reported, using the mean value of each of the remaining peaks.

The automated apparatus 102 is adapted to require calibration after a predetermined number, here 10, of analytical runs. In this regard, after the reporting of each of modules 312, 317, 322 or 328, a counter is incremented and module 330 determines whether or not a calibration run is necessary.

It will be appreciated that the instrument 102 may be readily used by unskilled personnel for field analysis of PCB's. In the preparation of dielectric fluid and other oil samples for analysis, a measured amount of the sample is mixed with predetermined quantities of concentrated sulfuric and an aliphatic hydrocarbon, such as hexane. The illustrated sample preparation kit contains an Eppendorf style pipet and disposable tips for use in sampling dielectric fluids. Once the sample has been removed from the transformer or other device containing the oil, it is sampled using the pipet to deliver 100 microliters of sample to a prefilled glass vial 10 containing predetermined quantities of hexane (e.g., 5 ml.) and concentrated sulfuric acid (e.g., 5 ml.). The screw cap of the vial, having an inert poly tetra-fluoroethylene covered septum for purposes of safety is next sealed tightly onto the vial, which is then vigorously shaken for approximately 30 seconds. The layers are then permitted to separate (for most samples this should only require a minute or so) into layers including a lower sulfuric acid layer and an upper hexane layer. The hexane layer sample is now ready for injection into the PCB analyzer 102.

In order to prepare a solid or more complex sample, such as soil, for analysis, a predetermined weight of the solid sample (e.g., one gram) is weighed into a solid sample vial, which in the illustrated embodiment has a volume of 40 ml. for a one gram sample size. A predetermined quantity of methanol from a premeasured vial is added to the sample vial 106, which is then capped and vigorously shaken for 30 seconds. The solid material is allowed to settle to the bottom of the vial, and a 1 milliliter sample of this solution (as a fluid sample) is withdrawn by syringe and placed in a vial containing predetermined quantities of hexane and sulfuric acid, as previously described with respect to dielectric fluid sample preparation. The methanol extracted PCB fluid sample is shaken vigorously for 30 seconds, and the layers are permitted to separate. Upon separation of the layers into an upper hexane layer and lower sulfuric acid, the hexane sample is ready for injection into the PCB analyzer 102, as previously described.

Prior to the analysis of samples, a calibration must be performed, as previously discussed in respect to the processing logic diagram of FIG. 3. The calibration serves two purposes: (1) it provides a system check to ensure that all parts of the instrument are functioning properly, and (2) it serves to compensate for any daily fluctuations in the response of the analyzer.

Calibration of the illustrated embodiment 102 is carried out by injecting a calibration standard mixture 107 which may be a solution of one part per million by weight of PCB mixture having the polychlorinated biphenyl isomer mixture corresponding to 54 weight percent of chlorine substitution (Aroclor 1254, a product of Monsanto Chemical Co.) in hexane, a two microliter aliquot of which may be injected into the analyzer in calibration mode. When the calibration analysis is successfully completed, which may take approximately 10 minutes, the instrument is ready for introduction of a sample solution. If the calibration can not be satisfactorily carried out, an appropriate message is printed out to the operator, as previously described.

To carry out an analysis, the SAMPLE button on the front panel of the instrument is pressed by the operator. A two microliter aliquot of the hexane extract from the sample cleanup and extraction procedure is then injected into the injection port of the analyzer 102. The PCB analyzer will automatically initiate an analysis cycle after injection and will compensate for sample-to-sample variation in injection time.

It will be appreciated by those of skill in the computer art that many programs may be prepared for microprocessor 124 to carry out the various steps set forth in the logic flow diagram of FIG. 3. Exemplary of such software for storage in the memory of the microprocessor are the programs listed following the description of the invention. The first is written in Motorola 6809 assembly language and functions to quantitate data while the second is written in a higher level Pascal language and operates as a driver to call subroutines found in the assembly language program, and also to perform calculations.

A general correlation of the routines and modules of the FIG. 3 flow diagram and the numbered steps of the programs is as follows: Upon operation of power "on"

control 146 routine 300 of the flow diagram is carried out which is listed on lines 152 through 298 of the assembly language program. The calibration routine 302 is listed on lines 223 through 237 of the Pascal program. Upon activation of start switch 150 and injecting the sample, the start enable module 304 is undertaken which is found on lines 284 through 294 of the assembly program. Routine 306, which converts the detector output to digital values and stores the retention times and the areas of the respective peaks from the sample run in memory 130, is found on lines 313 through 712 of the assembly program. Lines 376 through 389 of the assembly program relate to saturation routine 308.

If the output is not saturated, the microprocessor moves on to peak detection module 314, which is listed in lines 142 through 165 of the Pascal program, to check for the existence of peaks. The pattern similarity algorithm 316, which determines similarity of the stored sample data with predetermined stored PCB patterns stored in memory, corresponds to lines 279 through 289 of the Pascal program which calls lines 32 through 278 of that program. The low match routine 318 and the high match routine 320 are embodied in lines 155 through 165 of the Pascal program. The low match routine directs the printer to report the absence of PCBs by module 317 (assembly program lines 825 through 828) while the high match routine causes the printer to advise of the need for further laboratory analysis of the sample via subroutine 322 (Pascal program line 272). If there is found to be a high cosine theta match with any of the stored standard PCB vectors, then module 324, Pascal program lines 239 through 263, determines the quantitative amount of the PCB sample. Module 326, assembly program lines 714 through 791, functions to eliminate "outlying" values from the unknown sample concentration tables generated by subroutine 324. The report module 328 is listed on lines 265 through 276 of the Pascal program. Finally, the recalibration or "10th run" subroutine 330 corresponds to lines 255 and 256 of the assembly language program.

While the present invention has been described for one particular embodiment, it will be appreciated that various modifications may be made within the spirit and scope of the present disclosure.

What is claimed is:

```
00002                          OPT    NOG, NOS, PAG
00003          ***********************************************************
00004          *
00005          *  PURPOSE:
00006          *     THIS FIRMWARE PROGRAM CONTROLS ALL FUNCTIONS OF THE S-CUBED
00007          *     PCB MONITOR.  IT IS DESIGNED TO RUN ON THE S-CUBED SINGLE
00008          *     BOARD MICROCOMPUTER USING THE S-CUBED GARBAGE CARD.  THE
00009          *     SYSTEM CONTAINS A 6809 MICROPROCESSOR, 4 PARALLEL I/O PORTS,
00010          *     1 SERIAL I/O PORT, AND AN ANALOG/DIGITAL CONVERTER.  THE
00011          *     ADDRESS MAP FOR THE MACHINE APPEARS BELOW.  PERIPHERAL
00012          *     EQUIPMENT TO BE USED AND/OR CONTROLLED INCLUDES FRONT PANEL
00013          *     SWITCHES, INDICATOR LAMPS, A PRINTER, AND THE GAS CHROMATOGRAPH
00014          *     ELECTROMETER WHICH IS MONITORED VIA THE ADC.
00015          *
00016          *  ADDRESS ASSIGNMENTS
00017          *     RAM MEMORY              0000-0800
00018          *     PIA#1 A DATA            AF00
00019          *     PIA#1 B DATA            AF01
00020          *     PIA#1 A CONTROL         AF02
00021          *     PIA#1 B CONTROL         AF03
00022          *     PIA#2 A DATA            AF10
00023          *     PIA#2 B DATA            AF11
00024          *     PIA#2 A CONTROL         AF12
00025          *     PIA#2 B CONTROL         AF13
00026          *     TIMER                   AF20
00027          *     ADC                     AF40
00028          *     DAC                     AF50
00029          ***********************************************************
00030
00031          ***********************************************************
00032          *
00033          *  SWITCHES:
00034          *     FRONT PANEL SWITCHES ARE READ ON PIA#1 SIDE B.
00035          *
00036          *  INDICATOR LAMPS:
00037          *     THE 'ARM', 'CALIBRATE', 'ANALIZING', 'PRINT TEMP. ', 'POWER'
00038          *     LAMPS AND THE OVEN ON/OFF ARE CONTROLLED BY SIX OUTPUT LINES
00039          *     ON PIA#1 SIDE B.
00040          *
00041          *  PRINTER:
00042          *     ALL 8 OUTPUT LINES ON PIA#2 SIDE B ARE USED TO PROVIDE DATA
00043          *     TO THE PRINTER.  IN ADDITION THE TWO CONTROL LINES ON PIA#2
00044          *     SIDE B ARE USED FOR HANDSHAKE PURPOSES.
00045          *
00046          ***********************************************************
00047
00049          ***********************************************************
00050          *
00051          *  SYSTEM EQUATES
00052          *
00053          ***********************************************************
00054          *
00055   E000   A PGMROM EQU    $E000     ADDR OF PROGRAM ROM
00056   0000   A RAM    EQU    $0000     START ADDR OF RAM
00057   0400   A RAME   EQU    1024      1024 BYTES OF RAM IN SYSTEM
00058   AF00   A PIA1AD EQU    $AF00     PIA #1 A DATA
```

```
00059         AF01    A PIA1BD EQU    $AF01           PIA #1 B DATA
00060         AF02    A PIA1AC EQU    $AF02           PIA #1 A CONTROL
00061         AF03    A PIA1BC EQU    $AF03           PIA #1 B CONTROL
00062         AF10    A PIA2AD EQU    $AF10           PIA #2 A DATA
00063         AF11    A PIA2BD EQU    $AF11           PIA #2 B DATA
00064         AF12    A PIA2AC EQU    $AF12           PIA #2 A CONTROL
00065         AF13    A PIA2BC EQU    $AF13           PIA #2 B CONTROL
00066         AF21    A TIMEST EQU    $AF21           TIMER STATUS
00067         AF20    A TIME1C EQU    $AF20           TIMER-1 CONTROL
00068         AF21    A TIME2C EQU    $AF21           TIMER-2 CONTROL
00069         AF20    A TIME3C EQU    $AF20           TIMER-3 CONTROL
00070         AF22    A TIME1D EQU    $AF22           TIMER-1 DATA
00071         AF24    A TIME2D EQU    $AF24           TIMER-2 DATA
00072         AF26    A TIME3D EQU    $AF26           TIMER-3 DATA
00073         AF30    A ACIAD  EQU    $AF30           ACIA DATA
00074         AF31    A ACIAC  EQU    $AF31           ACIA CONTROL
00075         AF40    A ADC    EQU    $AF40           ANALOG-DIGITAL DATA
00076         AF50    A DAC    EQU    $AF50           DIGITAL-ANALOG CONVERTER
00077                 *   LAMPS AND SWITCHES
00078         0010    A LMPSMP EQU    $10
00079         0008    A LMPCAL EQU    $08
00080         0002    A LMPPRT EQU    $02
00081         0004    A LMPANA EQU    $04
00082         0040    A SWPRNT EQU    $40
00083         0020    A SWSMPL EQU    $20
00084         0080    A SWCAL  EQU    $80
00085         0001    A POVEN  EQU    $01
00086                 *   PCB MONITOR CONSTANTS
00087         01E0    A T2MIN  EQU    480             TWO MINUTES IN 4THS OF A SECOND
00088         0960    A T10MIN EQU    2400            10 MINUTES IN 4THS OF A SECOND
00089         0083    A MAXTMP EQU    $0083           MAXIMUM ALLOWABLE TEMPERATURE
00090         004F    A MINTMP EQU    $004F           MINIMUM OPERABLE OVEN
00091         0095    A TMPOFF EQU    149             A-D TEMPERATURE OFFSET
00092         0080    A DACMSK EQU    %10000000       INITIAL DAC MASK
00093         FF7F    A DACHI  EQU    $FF7F           OVER-RANGE ON DAC
00094         0008    A DACTIM EQU    8               WAIT TIME FOR DAC CALIBRATION
00095         0010    A DACMIN EQU    $10
00096                 *   PRINTER CONSTANTS
00097         000D    A CR     EQU    $0D
00098         000A    A LF     EQU    $0A
00099         0004    A EOT    EQU    $04
00100         0000    A NUL    EQU    $00
00101                 *   ANALYS CONSTANTS
00102         0200    A BUFLEN EQU    512
00103         0100    A BUFLO2 EQU    BUFLEN/2
00104         0032    A INTLEN EQU    50              BE CAREFUL ABOUT INTLO2!!!!
00105         0019    A INTLO2 EQU    INTLEN/2
00106         0018    A SLPLEN EQU    24
00107         0006    A SMOLEN EQU    6
00108         003C    A SOLTHR EQU    60              SOLVENT THRESHOLD
00109         006E    A SLPTHR EQU    110             DELTA SLOPE THRESHOLD
00110         0006    A PEKTHR EQU    6               PEAK-HEIGHT THRESHOLD
00111         0100    A INTTHR EQU    $100            INTEGRAL THRESHOLD
00112         0060    A WAITIM EQU    $60             WAIT FOR START OF INTEGRATION
00113         000A    A NCAL   EQU    10              NUMBER OF SAMPLES BETWEEN CALIBRATIONS
00114
00116                 ****************************************************************
00117                 *
00118                 *   EXTERNAL DEFINITIONS
00119                 *
00120                 ****************************************************************
00121                         XDEF    INITIA
00122                         XDEF    POLMON
00123                         XDEF    CHKRAT
00124                         XDEF    DEV05
00125                         XDEF    ERROR
00126                         XDEF    CALBRT
00127                         XDEF    CALRUN
00128                         XDEF    RAWDAT
00129                         XDEF    NUNK
00130                         XDEF    SCALE
00131                         XDEF    RNAME
00132                         XDEF    RMATCH
00133                         XDEF    RMEAN
00134                         XDEF    RDIFF
00135                         XDEF    NUMRAT
00136                         XDEF    RATIOS
00137                         XDEF    PRTNOR
00138                         XDEF    PRTCOM
00139                         XDEF    PRTRES
00140                         XDEF    PRTLOF
00141                         XDEF    PRTSMP
00142                         XDEF    PRTCAL
00143                 *   AND EXTERNAL REFERENCES
00144                         XREF    START
00145
```

```
00147          ***********************************************************************
00148          *
00149          *    SPECIAL POWER UP RESET FOR PCB MONITOR
00150          *
00151          ***********************************************************************
00152P 0000 34  60        A  INITIA PSHS   U,Y
00153P 0002 1A  50        A         ORCC   #$50        DISABLE IRQ AND FIRQ INTERRUPTS
00154P 0004 7F  0026      D         CLR    ERROR       ERROR FLAG
00155P 0007 7F  0025      D         CLR    NUMSMP      NUMBER OF PREVIOUS SAMPLES
00156P 000A 7F  AF50      A         CLR    DAC
00157P 000D 8E  AF00      A         LDX    #PIA1AD     -> PIA #1
00158P 0010 86  06        A         LDA    #%00000110
00159P 0012 A7  02        A         STA    2,X         PIA1AC-CA1 = CLOCK
00160P 0014 6F  03        A         CLR    3,X
00161P 0016 86  1F        A         LDA    #$1F
00162P 0018 A7  01        A         STA    1,X         PIA1BD = LAMPS/SWITCHES
00163P 001A A7  03        A         STA    3,X         PIA1BC-CB1/CB2 = NOT USED
00164P 001C 6F  01        A         CLR    1,X         TURN OFF ALL LAMPS
00165P 001E 30  88 10     A         LEAX   16,X        -> PIA #2
00166P 0021 6F  03        A         CLR    3,X
00167P 0023 86  7F        A         LDA    #$7F
00168P 0025 A7  01        A         STA    1,X         PIA2BD = PRINTER DATA
00169P 0027 86  36        A         LDA    #$36
00170P 0029 A7  03        A         STA    3,X         PIA2BC = PRINTER HAND-SHAKE
00171P 002B 8E  AF20      A         LDX    #TIME1C     ->6840--INITIALIZE TIMERS
00172P 002E 86  01        A         LDA    #$01
00173P 0030 A7  01        A         STA    1,X         SET CR2 TO WRITE CR1
00174P 0032 86  82        A         LDA    #$82        SET CR1 MODE
00175P 0034 A7  84        A         STA    0,X         (OUTPUT,CONTINUOUS 16, INTERNAL CLOCK)
00176P 0036 86  84        A         LDA    #$84        SET CR2 MODE
00177P 0038 A7  01        A         STA    1,X         (OUTPUT,CONTINUOUS, DUAL 8, EXTERNAL CLOCK)
00178P 003A 86  29        A         LDA    #$29        SET CR3 MODE
00179P 003C A7  84        A         STA    0,X         (FREQUENCY COMPARISON, 16, EXTERNAL, PRESCALE)
00180P 003E CC  1869      A         LDD    #$1869
00181P 0041 ED  02        A         STD    2,X         WRITE #1 LATCH
00182P 0043 CC  0304      A         LDD    #$0304
00183P 0046 ED  04        A         STD    4,X         WRITE #2 LATCH
00184P 0048 CC  FFFF      A         LDD    #$FFFF
00185P 004B ED  06        A         STD    6,X         WRITE #3 LATCH
00186                       *
00187                       *       WAIT FOR OVEN TEMPERATURES TO COME UP
00188                       *
00189P 004D 8E  0879      P         LDX    #MOVNON     OVEN ON MESSAGE
00190P 0050 17  04F0 0543           LBSR   PDATA
00191P 0053 17  05A1 05F7 RESETT LBSR    POLPRT       IS THERE A PRINT REQUEST?
00192P 0056 2D  FB   0053           BLT    RESETT      LOOP TIL THE TEMPS COME UP
00193P 0058 CC  0000      A         LDD    #T2MIN*0    EQUILIBRATE TEMPS FOR 4 MINUTES
00194P 005B FD  0021      D         STD    ELPSDT
00195P 005E 17  0596 05F7 RESETW LBSR    POLPRT
00196P 0061 2E  1C   007F          BGT    ABORT       ON TEMP OVERFLOW, ABORT
00197P 0063 7D  AF02      A         TST    PIA1AC      CLOCK
00198P 0066 2A  F6   005E          BPL    RESETW
00199P 0068 B6  AF00      A         LDA    PIA1AD      DUMMY READ
00200P 006B FC  0021      D         LDD    ELPSDT
00201P 006E 83  0001      A         SUBD   #1
00202P 0071 FD  0021      D         STD    ELPSDT      DECREMENT TIMER
00203P 0074 2E  E8   005E          BGT    RESETW
00204                       *
00205                       *    READY
00206                       *
00207P 0076 8E  08A1      P         LDX    #WELCOM
00208P 0079 17  04C7 0543           LBSR   PDATA       PRINT A READY MESSAGE
00209P 007C 35  60        A         PULS   U,Y
00210P 007E 39                      RTS
00211
00212                       ***********************************************************************
.00213                       *
00214                       *    SPECIAL SYSTEM SHUT-DOWN ON TEMPERATURE OVERFLOW
00215                       *
00216                       ***********************************************************************
00217                       *
00218P 007F 7F  AF01      A  ABORT  CLR    PIA1BD      TURN OFF EVERYTHING
00219P 0082 8E  0811      P         LDX    #XSTEMP     PRINT EXCESS TEMPERATURE MESSAGE
00220P 0085 17  04BB 0543           LBSR   PDATA
00221P 0088 17  0672 06FD           LBSR   PRTTMP      PRINT THE CURRENT TEMPERATURES
00222P 008B 17  0703 0791 ABORT1 LBSR    DELAY
00223P 008E 86  02        A         LDA    #LMPPRT     TOGGLE THE PRINT LAMP
00224P 0090 17  06F7 078A           LBSR   TGLBIT
00225P 0093 17  0361 05F7           LBSR   POLPRT
00226P 0096 2E  F3   008B          BGT    ABORT1      LOOP TIL TEMPS FALL ENOUGH
00227P 0098 86  02        A         LDA    #LMPPRT     TURN ON 'PRINT' LAMP
00228P 009A 17  06DE 077B           LBSR   SETBIT
00229P 009D 86  40        A  ABORT2 LDA    #SWPRNT
00230P 009F 17  06D5 0777           LBSR   CHKBIT      HAS THERE BEEN A PRINT REQUEST?
00231P 00A2 27  F9   009D          BEQ    ABORT2
00232P 00A4 17  0656 06FD           LBSR   PRTTMP      PRINT TEMPS
00233P 00A7 7C  0026      D         INC    ERROR       SET ERROR FLAG
00234P 00AA 35  60        A         PULS   U,Y
```

```
00235P 00AC 39                    RTS
00236                    *
00237P 00AD 3B           DUMRTI    RTI
00238                    *
00239P 00AE 8E  09D7   P DEVOS LDX  #MERROR
00240P 00B1 17  048F 0543     LBSR PDATA
00241P 00B4 6E  9F FFFE A     JMP  [$FFFE]
00242
00244           ****************************************************************
00245           *
00246           *   NOW WAIT FOR SOMETHING TO HAPPEN (LIKE 'ARM')
00247           *
00248           ****************************************************************
00249P 00B8 34  60     A POLMON PSHS U,Y
00250P 00BA 86  04     A POLMOA LDA  #LMPANA  TURN OFF ANALYZE LAMP
00251P 00BC 17  06C3 0782      LBSR CLRBIT
00252P 00BF 7D  0025   D       TST  NUMSMP
00253P 00C2 2E  09   00CD      BGT  POLMO1
00254P 00C4 8E  08B5   P       LDX  #REQCAL  RECALIBRATE EVERY N'TH TIME
00255P 00C7 17  0479 0543      LBSR PDATA
00256P 00CA 7F  0023   D       CLR  CALBRT
00257                    *
00258P 00CD 86  08     A POLMO1 LDA  #LMPCAL
00259P 00CF 7D  AF01   A       TST  PIA1BD   WAS 'CAL' PUSHED?
00260P 00D2 2B  08   00DC      BMI  POLMO2   IF SO, SET UP FOR CALIBRATION
00261P 00D4 17  06AB 0782      LBSR CLRBIT   ELSE, TURN OFF 'CALIBRATE' LAMP
00262P 00D7 7F  0024   D       CLR  CALRUN   SET FOR NON-CAL RUN
00263P 00DA 20  08   00E4      BRA  POLMO3
00264P 00DC 17  069C 077B POLMO2 LBSR SETBIT TURN ON 'CAL' LAMP
00265P 00DF 86  01     A       LDA  #1
00266P 00E1 B7  0024   D       STA  CALRUN   SET FOR CALIBRATION-TYPE RUN
00267P 00E4 86  20     A POLMO3 LDA  #SWSMPL
00268P 00E6 17  068E 0777      LBSR CHKBIT   WAS 'SAMPLE' PUSHED?
00269P 00E9 26  07   00F2      BNE  TIMER    LOOK FOR SAMPLE
00270                    *
00271P 00EB 17  0509 05F7      LBSR POLPR1   ELSE, POLL THE PRINT SWITCH
00272P 00EE 2E  8F   007F      BGT  ABORT    ON TEMP OVERFLOW, ABORT
00273P 00F0 20  DB   00CD      BRA  POLMO1   LOOP TIL 'SAMPLE'
00274                    *
00275                    *  GOT AN 'ARM', NOW TIME OUT
00276                    *
00277P 00F2 7D  0024   D TIMER  TST  CALRUN   ARE WE CALIBRATING?
00278P 00F5 26  0A   0101      BNE  TIMEA
00279P 00F7 7D  0023   D       TST  CALBRT   HAVE WE BEEN CALIBRATED?
00280P 00FA 26  0A   0106      BNE  TIME1
00281P 00FC 7F  0025   D       CLR  NUMSMP
00282P 00FF 20  B9   00BA      BRA  POLMOA   AND GO AWAY
00283                    *
00284P 0101 17  053A 063E TIMEA LBSR SETDAC   ZERO DAC
00285P 0104 26  B4   00BA      BNE  POLMOA
00286P 0106 86  10     A TIME1  LDA  #LMPSMP  TURN ON 'SAMPLE' LAMP
00287P 0108 17  0670 077B      LBSR SETBIT
00288P 010B 8E  08CC   P       LDX  #INJECT
00289P 010E 17  0432 0543      LBSR PDATA
00290P 0111 17  067D 0791      LBSR DELAY
00291P 0114 B6  AF00   A       LDA  PIA1AD   DUMMY READ CLEARS ...
00292P 0117 17  05AB 06C3      LBSR GETSOS   GO LOOK FOR SOLVENT PEAK
00293P 011A 26  0D   0129      BNE  COLECT   IF FOUND ONE, GO TO IT...
00294P 011C 86  10     A       LDA  #LMPSMP  TURN OUT 'SAMPLE'
00295P 011E 17  0661 0782      LBSR CLRBIT
00296P 0121 8E  0927   P       LDX  #NOSOLV
00297P 0124 17  041C 0543      LBSR PDATA    PRINT NO SOLVENT MESSAGE
00298P 0127 20  A4   00CD      BRA  POLMO1   AND GO AWAY
00299
00300
00302           ****************************************************************
00303           *
00304           *   COLLECT DATA — HERE'S WHERE WE GET GOING
00305           *
00306           ****************************************************************
00307
00308P 0129 86  04     A COLECT LDA  #LMPANA  TURN ON 'ANALYZE'
00309P 012B 8A  10     A       ORA  #LMPSMP  TURN OFF 'SAMPLE'
00310P 012D 17  065A 078A      LBSR TGLBIT
00311P 0130 17  065E 0791      LBSR DELAY
00312P 0133 7A  0025   D       DEC  NUMSMP
00313P 0136 CC  043A   D       LDD  #DATBUF  -> DATA BUFFER
00314P 0139 FD  0030   D       STD  DATPTR
00315P 013C B6  AF00   A       LDA  PIA1AD   DUMMY READ CLEARS CA1
00316P 013F 17  04C2 0604 COLECL LBSR GETTMP CHECK THE TEMPERATURES
00317P 0142 102E FF39 007F      LBGT ABORT   ON OVER-TEMP, ABORT
00318P 0146 17  055C 06A5      LBSR GETSMP
00319P 0149 BE  0030   D       LDX  DATPTR
00320P 014C ED  81     A       STD  ,X++
00321P 014E BF  0030   D       STX  DATPTR
00322P 0151 8C  16FA   D       CMPX #DATBFE
00323P 0154 2D  E9   013F      BLT  COLECL   CONTINUE, IF NOT FINISHED
00324                    *
```

```
00325P 0156 8E    0057    D           LDX     #INTBUF    SET BUFFERS TO GARBAGE
00326P 0159 CC    AAAA    A           LDD     #$AAAA
00327P 015C ED    81      A  COLECI   STD     ,X++
00328P 015E 8C    02A7    D           CMPX    #SMOBFE
00329P 0161 26    F9      015C        BNE     COLECI
00330P 0163 7F    0046    D           CLR     SMPCNT     INITIALIZE SOME STUFF FOR ANALYSIS
00331P 0166 7F    0047    D           CLR     SMPCNT+1
00332P 0169 8E    03D6    D           LDX     #VALBUF
00333P 016C BF    0034    D           STX     VALPTR
00334P 016F 7F    002F    D           CLR     MULTVF
00335P 0172 7F    0036    D           CLR     PREVAL
00336P 0175 7F    0037    D           CLR     PREVAL+1
00337P 0178 7F    003A    D           CLR     PEKVAL
00338P 017B 7F    003B    D           CLR     PEKVAL+1
00339P 017E 7F    003E    D           CLR     INTGRL
00340P 0181 7F    003F    D           CLR     INTGRL+1
00341P 0184 7F    004B    D           CLR     SCALE
00342P 0187 7F    004C    D           CLR     SCALE+1
00343P 018A 7F    004A    D           CLR     SCLINT
00344P 018D CC    0100    A           LDD     #INTTHR
00345P 0190 FD    0042    D           STD     INTMIN
00346P 0193 CC    02AA    D           LDD     #PEKBUF
00347P 0196 FD    0032    D           STD     PEKPTR
00348P 0199 8E    043A    D           LDX     #DATBUF
00349P 019C EC    81      A  COLECP   LDD     ,X++       NOW PROCESS THE DATA
00350P 019E 34    10      A           PSHS    X
00351P 01A0 8D    5C      01FE        BSR     PROCES
00352P 01A2 35    10      A           PULS    X
00353P 01A4 102E FED7 007F            LBGT    ABORT      ON OVER-TEMP, ABORT
00354P 01A8 8C    16FA    D           CMPX    #DATBFE
00355P 01AB 2D    EF      019C        BLT     COLECP     LOOP OVER ALL DATA
00356P 01AD 8E    0200    A           LDX     #BUFLEN
00357P 01B0 FC    0040    D  COLECF   LDD     LSTVAL     AND FLUSH THE BUFFERS
00358P 01B3 34    10      A           PSHS    X
00359P 01B5 8D    47      01FE        BSR     PROCES
00360P 01B7 35    10      A           PULS    X
00361P 01B9 102E FEC2 007F            LBGT    ABORT      IF TEMPS OVERFLOW
00362P 01BD 30    1F      A           LEAX    -1,X
00363P 01BF 26    EF      01B0        BNE     COLECF
00364                                 *
00365P 01C1 17    025B 041F           LBSR    CULPEK     CUL PEAK-INTEGRAL BUFFER
00366P 01C4 17    02B9 0480           LBSR    SETSCL     SET THE SCALE FACTOR
00367P 01C7 7D    004B    D           TST     SCALE
00368P 01CA 26    09      01D5        BNE     COLECE
00369P 01CC CC    55AA    A           LDD     #$55AA
00370P 01CF FD    0053    D           STD     RDIFF
00371P 01D2 35    60      A           PULS    U,Y
00372P 01D4 39                        RTS
00373                                 *
00374                                 *  COLLECT-DATA ERROR--'D' HOLDS TIME TO WAIT
00375                                 *
00376P 01D5 8E    098A    P  COLECE   LDX     #XSSMPL
00377P 01D8 17    0368 0543           LBSR    PDATA
00378P 01DB FC    1C20    A           LDD     T10MIN*3
00379P 01DE FD    0021    D  COLEC1   STD     ELPSDT     DELAY TIME
00380P 01E1 17    05AD 0791           LBSR    DELAY
00381P 01E4 86    04      A           LDA     #LMPANA    BLINK ANALYZE LAMP
00382P 01E6 17    05A1 078A           LBSR    TGLBIT
00383P 01E9 17    040B 05F7           LBSR    POLPRT
00384P 01EC 102E FE8F 007F            LBGT    ABORT
00385P 01F0 FC    0021    D           LDD     ELPSDT
00386P 01F3 83    0001    A           SUBD    #1
00387P 01F6 2E    E6      01DE        BGT     COLEC1
00388P 01F8 7F    0025    D           CLR     NUMSMP     ENSURE RECALIBRATION
00389P 01FB 16    FEBC 00BA           LBRA    POLMOA
00390
00392                                 ************************************************************************
00393                                 *
00394                                 *  BASELINE SUBTRACT AND INTEGRATION SUBROUTINES
00395                                 *
00396                                 ************************************************************************
00397                                 *
00398                                 *  PROCESS SAMPLE DATA
00399                                 *
00400P 01FE FD    02A5    D  PROCES   STD     SMOBFE-2   SAVE NEW RAW DATUM
00401P 0201 FC    0046    D           LDD     SMPCNT
00402P 0204 C3    0001    A           ADDD    #1
00403P 0207 FD    0046    D           STD     SMPCNT
00404P 020A 8D    0F      021B        BSR     SMOOTH
00405P 020C 8D    26      0234        BSR     VALUPD     UPDATE THE VALLEY BUFFER
00406P 020E 17    0095 02A6           LBSR    BASLNS     GO PUT A NEW BASELINE SUBTRACTED DATUM IN BUFFER
00407P 0211 17    0131 0345           LBSR    INTGRT     INTEGRATE A PEAK
00408P 0214 17    01FB 0412           LBSR    SLIDEB     SLIDE THE BUFFERS LEFT
00409P 0217 17    03EA 0604           LBSR    GETTMP     CHECK TEMPERATURES
00410P 021A 39                        RTS                RETURN FOR NOW
00411                                 *
00412                                 *  SMOOTH THE DATA BY TAKING WEIGHTED SEVEN SAMPLE AVERAGE
00413                                 *
00414P 021B 8E    02A1    D  SMOOTH   LDX     #SLPBFE
```

```
00415P 021E EC   84            A            LDD    ,X         ONE TIMES
00416P 0220 1083 AAAA          A            CMPD   #$AAAA     IS THE DATUM BOGUS ?
00417P 0224 27   0A   0230                  BEQ    SMOOT1     YES
00418P 0226 E3   02            A            ADDD   2,X
00419P 0228 E3   04            A            ADDD   4,X
00420P 022A E3   02            A            ADDD   2,X
00421P 022C 44                              LSRA
00422P 022D 56                              RORB
00423P 022E 44                              LSRA
00424P 022F 56                              RORB
00425P 0230 FD   029F   D SMOOT1            STD    SLPBFE-2   SAVE AVERAGED DATUM
00426P 0233 39                              RTS
00427                                 *
00428                                 * UPDATE THE VALLEY BUFFER WITH DATA FROM RIGHT EDGE OF RAWBUF
00429                                 *
00430P 0234 BE   0034   D VALUPD            LDX    VALPTR
00431P 0237 FC   0046   D                   LDD    SMPCNT
00432P 023A ED   81            A            STD    ,X++
00433P 023C 1083 0960          A            CMPD   #T10MIN
00434P 0240 2E   3F   0281                  BGT    VALUPN
00435P 0242 FC   0287   D                   LDD    RAWBFE-2
00436P 0245 ED   84            A            STD    ,X         SAVE POTENTIAL VALLEY
00437P 0247 8E   026F   D                   LDX    #RAWBFE-26
00438P 024A 8D   41   028D                  BSR    ISLOWV     WELL, IS IT A VALLEY?
00439P 024C 26   33   0281                  BNE    VALUPN     NO
00440P 024E 1083 AAAA          A            CMPD   #$AAAA     DO WE HAVE REAL DATA YET?
00441P 0252 27   2C   0280                  BEQ    VALUPX
00442P 0254 FD   0040   D                   STD    LSTVAL     SAVE VALLEY
00443P 0257 BE   0034   D                   LDX    VALPTR
00444P 025A 8C   03D7   D                   CMPX   #VALBUF+1
00445P 025D 25   1C   027B                  BLO    VALUP2     ALWAYS SAVE FIRST VALLEY
00446P 025F EC   84            A            LDD    ,X
00447P 0261 A3   1C            A            SUBD   -4,X
00448P 0263 1083 0001          A            CMPD   #1         ARE THE VALLEYS ADJACENT?
00449P 0267 26   12   027B                  BNE    VALUP2
00450P 0269 7D   002F   D                   TST    MULTVF     IS THIS THE FIRST MULTIPLE?
00451P 026C 27   0A   0278                  BEQ    VALUP1
00452P 026E EC   84            A            LDD    ,X
00453P 0270 ED   1C            A            STD    -4,X
00454P 0272 EC   02            A            LDD    2,X
00455P 0274 ED   1E            A            STD    -2,X
00456P 0276 30   1C            A            LEAX   -4,X       OVER-WRITE A MULTIPLE
00457P 0278 7C   002F   D VALUP1            INC    MULTVF
00458P 027B 30   04            A VALUP2     LEAX   4,X
00459P 027D BF   0034   D                   STX    VALPTR
00460P 0280 39                 VALUPX       RTS
00461                                 *
00462P 0281 BE   0034   D VALUPN            LDX    VALPTR
00463P 0284 FC   0040   D                   LDD    LSTVAL     COPY THE LAST VALLEY
00464P 0287 ED   02            A            STD    2,X
00465P 0289 7F   002F   D                   CLR    MULTVF     CLEAR THE MULTIPLE VALLEY FLAG
00466P 028C 39                              RTS
00467                                 *
00468                                 * IS THE CENTER OF A 15 SAMPLE WNDOW THE SMALLEST DATUM?
00469                                 *
00470P 028D EC   88   18       A ISLOWV     LDD    24,X       LOOK AT MIDDLE OF WINDOW
00471P 0290 31   88   30       A            LEAY   48,X       CALC THE ENDIND LOCATION
00472P 0293 34   20            A            PSHS   Y
00473P 0295 10A3 81            A ISLOWL     CMPD   ,X++
00474P 0298 2E   07   02A1                  BGT    ISLOWN     NOT THE LOWEST
00475P 029A AC   E4            A            CMPX   0,S
00476P 029C 26   F7   0295                  BNE    ISLOWL
00477P 029E 35   20            A            PULS   Y
00478P 02A0 39                              RTS
00479P 02A1 35   20            A ISLOWN     PULS   Y
00480P 02A3 1C   FB            A            ANDCC  #$FB       CLEAR THE Z FLAG
00481P 02A5 39                              RTS
00482                                 *
00483                                 * CALCULATE ONE NEW BASELINE SUBTRACTED DATUM AND SAVE IT
00484                                 *
00485P 02A6 FC   0046   D BASLNS            LDD    SMPCNT     GET CURRENT SAMPLE COUNT
00486P 02A9 83   0100          A            SUBD   #BUFLO2    ADJUST IT FOR BUFFER PROPAGATION TIME
00487P 02AC FD   0048   D                   STD    SMPTIM
00488P 02AF 2B   3E   02EF                  BMI    BASLNX
00489P 02B1 7F   0044   D                   CLR    LOWINT
00490P 02B4 7F   0045   D                   CLR    LOWINT+1
00491P 02B7 BE   0034   D                   LDX    VALPTR
00492P 02BA 8C   03DB   D                   CMPX   #VALBUF+5
00493P 02BD 25   2A   02E9                  BLO    BASLN3
00494P 02BF 8E   03D6   D                   LDX    #VALBUF
00495P 02C2 10A3 04            A            CMPD   4,X        HAS THE RIGHT VALLEY MOVED TO THE LEFT
00496P 02C5 2D   18   02DF                  BLT    BASLN2
00497P 02C7 EC   04            A BASLNA     LDD    4,X        SHIFT VALLEY BUFFER DOWN
00498P 02C9 ED   81            A            STD    ,X++
00499P 02CB EC   04            A            LDD    4,X
00500P 02CD ED   81            A            STD    ,X++
00501P 02CF BC   0034   D                   CMPX   VALPTR
00502P 02D2 2F   F3   02C7                  BLE    BASLNA
00503P 02D4 BE   0034   D                   LDX    VALPTR
```

```
00504P 02D7 30    1C        A             LEAX   -4,X
00505P 02D9 BF    0034      D             STX    VALPTR
00506P 02DC 8E    03D6      D             LDX    #VALBUF
00507P 02DF 8D    OF    02F0 BASLN2       BSR    INTERP
00508P 02E1 FC    0089      D             LDD    RAWBUF
00509P 02E4 B3    0044      D             SUBD   LOWINT
00510P 02E7 2C    03    02EC              BGE    BASLN4
00511P 02E9 CC    0000      A BASLN3      LDD    #0
00512P 02EC FD    0087      D BASLN4      STD    INTBFE-2 SAVE BS DATUM FOR PEAK INTEGRATION
00513P 02EF 39                BASLNX      RTS
00514                                     *
00515                                     * SUBROUTINE FOR FINDING A BASELINE INTERPOLATE AT THE MIDPOINT
00516                                     *
00517P 02F0 7F    0008      D INTERP      CLR    SIGN     KEEP TRACK OF SIGN
00518P 02F3 EC    06        A             LDD    6,X      FIND AN INTERPOLATED BASLINE VALUE
00519P 02F5 A3    02        A             SUBD   2,X
00520P 02F7 2A    08    0301              BPL    INTER1   RESULT WAS POSITIVE
00521P 02F9 43                            COMA
00522P 02FA 53                            COMB
00523P 02FB C3    0001      A             ADDD   #1
00524P 02FE 73    0008      D             COM    SIGN
00525P 0301 108E  0000      D INTER1      LDY    #MREGOH  ->MATH REGS
00526P 0305 ED    24        A             STD    4,Y
00527P 0307 FC    0048      D             LDD    SMPTIM
00528P 030A A3    84        A             SUBD   ,X
00529P 030C 2A    08    0316              BPL    INTER2
00530P 030E 43                            COMA
00531P 030F 53                            COMB
00532P 0310 C3    0001      A             ADDD   #1
00533P 0313 73    0008      D             COM    SIGN
00534P 0316 ED    26        A INTER2      STD    6,Y
00535P 0318 17    04C7  07E2              LBSR   MULT16
00536P 031B EC    04        A             LDD    4,X
00537P 031D A3    84        A             SUBD   ,X
00538P 031F 2A    08    0329              BPL    INTR2A
00539P 0321 43                            COMA
00540P 0322 53                            COMB
00541P 0323 C3    0001      A             ADDD   #1
00542P 0326 73    0008      D             COM    SIGN
00543P 0329 ED    24        A INTR2A      STD    4,Y
00544P 032B 17    046C  079A              LBSR   DIVIDE
00545P 032E 17    0498  07C9              LBSR   ROUND    ROUND THE RESULT OF THE DIVIDE
00546P 0331 EC    02        A             LDD    2,X
00547P 0333 7D    0008      D             TST    SIGN     WAS THE SLOPE NEGATIVE?
00548P 0336 27    07    033F              BEQ    INTER3   NO
00549P 0338 63    22        A             COM    2,Y
00550P 033A 63    23        A             COM    3,Y
00551P 033C C3    0001      A             ADDD   #1
00552P 033F E3    22        A INTER3      ADDD   2,Y
00553P 0341 FD    0044      D             STD    LOWINT
00554P 0344 39                            RTS
00555                                     *
00556                                     * INTEGRATE PEAKS
00557                                     *
00558P 0345 FC    0048      D INTGRT      LDD    SMPTIM   CONTAINS SAMPLE TIME AT RAWBUF
00559P 0348 83    000C      A             SUBD   #INTLO2/2 UPDATE IT TO SHOW TIME AT INTEGRATION POINT
00560P 034B FD    0048      D             STD    SMPTIM
00561P 034E ED    9F 0032   D             STD    [PEKPTR] STUFF A DUMMY TIME IN THE BUFFER
00562P 0352 83    000C      A             SUBD   #INTLO2/2
00563P 0355 83    0060      A             SUBD   #WAITIM  DON'T INTEGRATE THE SOLVENT PEAK
00564P 0358 102D  0082  03DE               LBLT   INTGRX   IF NO DATA YET, QUIT
00565P 035C FC    006F      D             LDD    INTMID   WE CONSIDER THE MIDDLE DATUM
00566P 035F 1083  0006      A             CMPD   #PEKTHR  IS IT ABOVE THRESHOLD?
00567P 0363 2D    41    03A6              BLT    INTGR1   IF NOT, SAVE WHAT WE HAVE AND QUIT
00568P 0365 8E    0057      D             LDX    #INTBUF
00569P 0368 17    FF22  028D              LBSR   ISLOWV   IS IT THE LOWEST POINT IN THE AREA?
00570P 036B 27    39    03A6              BEQ    INTGR1   YES
00571P 036D FC    006F      D             LDD    INTMID
00572P 0370 FD    0044      D             STD    LOWINT
00573P 0373 B6    004A      D             LDA    SCLINT
00574P 0376 4D                INTGRA      TSTA           SCALE THE DATUM
00575P 0377 27    09    0382              BEQ    INTGRB
00576P 0379 74    0044      D             LSR    LOWINT
00577P 037C 76    0045      D             ROR    LOWINT+1
00578P 037F 4A                            DECA
00579P 0380 20    F4    0376              BRA    INTGRA
00580P 0382 FC    003E      D INTGRB      LDD    INTGRL
00581P 0385 F3    0044      D             ADDD   LOWINT   ADD THE SCALED DATUM
00582P 0388 2A    05    038F              BPL    INTGRC
00583P 038A 44                            LSRA
00584P 038B 56                            RORB
00585P 038C 7C    004A      D             INC    SCLINT
00586P 038F FD    003E      D INTGRC      STD    INTGRL
00587P 0392 FC    006F      D             LDD    INTMID
00588P 0395 10B3  003A      D             CMPD   PEKVAL
00589P 0399 2D    43    03DE              BLT    INTGRX   IF THIS PEAK IS SMALLER THAN A PREVIOUS ONE, QUIT
00590P 039B FD    003A      D             STD    PEKVAL   ELSE, UPDATE
00591P 039E FC    0048      D             LDD    SMPTIM
00592P 03A1 FD    003C      D             STD    PEKTIM
00593P 03A4 20    38    03DE              BRA    INTGRX
```

```
00594P 03A6 FC    003A    D INTGR1 LDD    PEKVAL    HAVE WE SEEN A PEAK?
00595P 03A9 27    18      03C3      BEQ    INTGR2    NO
00596P 03AB 8D    32      03DF      BSR    SCALEM
00597P 03AD BE    0032    D         LDX    PEKPTR    ELSE, SAVE IT
00598P 03B0 FC    003C    D         LDD    PEKTIM
00599P 03B3 ED    81      A         STD    ,X++
00600P 03B5 FC    003E    D         LDD    INTGRL
00601P 03B8 ED    81      A         STD    ,X++
00602P 03BA 10B3  0042    D         CMPD   INTMIN
00603P 03BE 2F    03      03C3      BLE    INTGR2    DON'T SAVE TINY INTEGRAL
00604P 03C0 BF    0032    D         STX    PEKPTR
00605P 03C3 7F    003A    D INTGR2 CLR    PEKVAL    CLEAR OLD PEAK VALUE
00606P 03C6 7F    003B    D         CLR    PEKVAL+1
00607P 03C9 7F    003E    D         CLR    INTGRL    CLEAR THE ACCUMULATED INTEGRAL
00608P 03CC 7F    003F    D         CLR    INTGRL+1
00609P 03CF 7F    004A    D         CLR    SCLINT
00610P 03D2 FC    0048    D         LDD    SMPTIM
00611P 03D5 FD    0038    D         STD    PREVTM    UPDATE THE PREVIOUS VALLEY TIME
00612P 03D8 FC    006F    D         LDD    INTMID
00613P 03DB FD    0036    D         STD    PREVAL    UPDATE PREVIOUS VALLEY INFORMATION
00614P 03DE 39                      INTGRX RTS
00615                                *
00616                                *    SCALE THE INTEGRALS ON OVERFLOW
00617                                *
00618P 03DF B6    004A    D SCALEM LDA    SCLINT
00619P 03E2 B1    004C    D         CMPA   SCALE+1
00620P 03E5 27    2A      0411      BEQ    SCALEX
00621P 03E7 2D    1B      0404      BLT    SCALE2
00622P 03E9 8E    02AC    D         LDX    #PEKBUF+2
00623P 03EC EC    84      A SCALE1 LDD    ,X
00624P 03EE 44                      LSRA
00625P 03EF 56                      RORB
00626P 03F0 ED    84      A         STD    ,X
00627P 03F2 30    04      A         LEAX   4,X
00628P 03F4 BC    0032    D         CMPX   PEKPTR
00629P 03F7 2D    F3      03EC      BLT    SCALE1    DO ALL PREVIOUS PEAKS
00630P 03F9 7C    004C    D         INC    SCALE+1
00631P 03FC 74    0042    D         LSR    INTMIN
00632P 03FF 76    0043    D         ROR    INTMIN+1
00633P 0402 20    DB      03DF      BRA    SCALEM
00634P 0404 FC    003E    D SCALE2 LDD    INTGRL
00635P 0407 44                      LSRA
00636P 0408 56                      RORB
00637P 0409 FD    003E    D         STD    INTGRL
00638P 040C 7C    004A    D         INC    SCLINT
00639P 040F 20    CE      03DF      BRA    SCALEM
00640P 0411 39                      SCALEX RTS
00641                                *
00642                                *    SLIDE TEMP BUFFERS LEFT TO GET READY FOR NEXT SAMPLE
00643                                *
00644P 0412 8E    0057    D SLIDEB LDX    #INTBUF   -> DATA BUFFER
00645P 0415 EC    02      A SLDLOP LDD    2,X
00646P 0417 ED    81      A         STD    ,X++
00647P 0419 8C    02A5    D         CMPX   #SMOBFE-2
00648P 041C 26    F7      0415      BNE    SLDLOP
00649P 041E 39                      RTS
00650                                *
00651                                *    CUL PEAK-INTEGRAL BUFFER IF TOO MANY PEAKS
00652                                *
00653P 041F FC    0032    D CULPEK LDD    PEKPTR
00654P 0422 83    02AA    D         SUBD   #PEKBUF
00655P 0425 47                      ASRA
00656P 0426 56                      RORB
00657P 0427 47                      ASRA
00658P 0428 56                      RORB
00659P 0429 FD    0055    D         STD    NUNK
00660P 042C 27    51      047F      BEQ    CULPEX
00661P 042E 1083  0014    A         CMPD   #20
00662P 0432 2F    2F      0463      BLE    CULPE4
00663P 0434 8E    02AA    D         LDX    #PEKBUF
00664P 0437 31    84      A         LEAY   ,X        INITIALIZE
00665P 0439 EC    02      A CULPE1 LDD    2,X       LOOP TO FIND SMALLEST PEAK
00666P 043B 10A3  22      A         CMPD   2,Y
00667P 043E 2C    02      0442      BGE    CULPE2
00668P 0440 31    84      A         LEAY   ,X        POINT TO SMALLER PEAK
00669P 0442 30    04      A CULPE2 LEAX   4,X
00670P 0444 BC    0032    D         CMPX   PEKPTR
00671P 0447 2D    F0      0439      BLT    CULPE1
00672P 0449 30    24      A         LEAX   4,Y
00673P 044B EC    81      A CULPE3 LDD    ,X++      CRUNCH OUT SMALL PEAKS
00674P 044D ED    A1      A         STD    ,Y++
00675P 044F EC    81      A         LDD    ,X++
00676P 0451 ED    A1      A         STD    ,Y++
00677P 0453 BC    0032    D         CMPX   PEKPTR
00678P 0456 2D    F3      044B      BLT    CULPE3
00679P 0458 FC    0032    D         LDD    PEKPTR
00680P 045B 83    0004    A         SUBD   #4
00681P 045E FD    0032    D         STD    PEKPTR    DECREMENT NUMBER OF PEAKS
00682P 0461 20    BC      041F      BRA    CULPEK
```

```
00683P 0463 8E   0057    D CULPE4 LDX     #RAWDAT
00684P 0466 108E 02AA    D        LDY     #PEKBUF
00685P 046A EC   A1      A CULPE5 LDD     ,Y++         MOVE PEAK DATA
00686P 046C ED   81      A        STD     ,X++
00687P 046E EC   A1      A        LDD     ,Y++
00688P 0470 ED   81      A        STD     ,X++
00689P 0472 26   05   0479        BNE     CULPE6
00690P 0474 30   1C      A        LEAX    -4,X         IF TOO SMALL, SKIP IT
00691P 0476 7A   0056    D        DEC     NUNK+1
00692P 0479 10BC 0032    D CULPE6 CMPY    PEKPTR
00693P 047D 2D   EB   046A        BLT     CULPE5
00694P 047F 39                CULPEX RTS
00695                         *
00696                         *   SET THE SCALE FACTOR FOR PASCAL
00697                         *
00698P 0480 FC   004B    D SETSCL LDD     SCALE
00699P 0483 1083 0003    A        CMPD    #3
00700P 0487 2E   0D   0496        BGT     SETSCO
00701P 0489 86   01      A        LDA     #1
00702P 048B 5D                    TSTB
00703P 048C 27   04   0492        BEQ     SETSCX
00704P 048E 48             SETSC1 ASLA
00705P 048F 5A                    DECB
00706P 0490 26   FC   048E        BNE     SETSC1       CREATE PASCAL INTEGER
00707P 0492 B7   004C    D SETSCX STA     SCALE+1
00708P 0495 39                    RTS
00709                         *
00710P 0496 7C   004B    D SETSCO INC     SCALE
00711P 0499 39                    RTS                  ON OVERFLOW, SET FLAG
00712
00714                         ****************************************************
00715                         *
00716                         *   CHECK RATIOS FOR OUTSIDERS--CALLED FROM PASCAL
00717                         *
00718                         ****************************************************
00719P 049A 34   60      A CHKRAT PSHS    U,Y          FOR PASCAL
00720P 049C 8E   02AA    D        LDX     #RATIOS
00721P 049F 108E 0000    D        LDY     #MREGOH
00722P 04A3 CC   0000    A        LDD     #0
00723P 04A6 ED   A4      A        STD     ,Y
00724P 04A8 ED   22      A        STD     2,Y
00725P 04AA FC   02A8    D        LDD     NUMRAT       DIVISOR AND COUNT
00726P 04AD ED   24      A        STD     4,Y
00727P 04AF 34   04      A        PSHS    B
00728P 04B1 E6   84      A CHKRA1 LDB     ,X           GET EXPONENT
00729P 04B3 C5   40      A        BITB    #$40         IS IT NEGATIVE?
00730P 04B5 27   02   04B9        BEQ     CHKRA2
00731P 04B7 CA   80      A        ORB     #$80
00732P 04B9 1D             CHKRA2 SEX                  CREATE PROPER 2'S COMP
00733P 04BA E3   22      A        ADDD    2,Y
00734P 04BC ED   22      A        STD     2,Y          AND ACCUMULATE
00735P 04BE 30   04      A        LEAX    4,X
00736P 04C0 6A   E4      A        DEC     ,S
00737P 04C2 26   ED   04B1        BNE     CHKRA1
00738P 04C4 32   61      A        LEAS    1,S          POP STACK
00739P 04C6 7F   0008    D        CLR     SIGN
00740P 04C9 6D   22      A        TST     2,Y
00741P 04CB 2A   0A   04D7        BPL     CHKRA3       ENSURE POSITIVE DIVIDE
00742P 04CD 43                    COMA
00743P 04CE 53                    COMB
00744P 04CF C3   0001    A        ADDD    #1
00745P 04D2 73   0008    D        COM     SIGN
00746P 04D5 ED   22      A        STD     2,Y
00747P 04D7 17   02C0 079A CHKRA3 LBSR    DIVIDE
00748P 04DA 17   02EC 07C9        LBSR    ROUND
00749P 04DD 7D   0008    D        TST     SIGN
00750P 04E0 27   09   04EB        BEQ     CHKRA4
00751P 04E2 EC   22      A        LDD     2,Y          RESTORE SIGN
00752P 04E4 43                    COMA
00753P 04E5 53                    COMB
00754P 04E6 C3   0001    A        ADDD    #1
00755P 04E9 ED   22      A        STD     2,Y
00756P 04EB 8E   02AA    D CHKRA4 LDX     #RATIOS
00757P 04EE FC   02A8    D        LDD     NUMRAT
00758P 04F1 A6   84      A CHKRA5 LDA     ,X
00759P 04F3 85   40      A        BITA    #$40
00760P 04F5 27   02   04F9        BEQ     CHKRA6
00761P 04F7 8A   80      A        ORA     #$80         CREATE PROPER NEGATIVE
00762P 04F9 80   01      A CHKRA6 SUBA    #1
00763P 04FB A1   23      A        CMPA    3,Y
00764P 04FD 2F   04   0503        BLE     CHKRA7
00765P 04FF 8D   12   0513        BSR     CULRAT
00766P 0501 20   08   050B        BRA     CHKRA8
00767P 0503 8B   02      A CHKRA7 ADDA    #2
00768P 0505 A1   23      A        CMPA    3,Y
00769P 0507 2C   02   050B        BGE     CHKRA8
00770P 0509 8D   08   0513        BSR     CULRAT
```

```
00771P 050B 30    04          A CHKRA8 LEAX    4,X
00772P 050D 5A                         DECB
00773P 050E 26    E1    04F1    BNE    CHKRA5
00774P 0510 35    60          A .PULS  U,Y         FOR PASCAL
00775P 0512 39                         RTS
00776                          *
00777                          *   CULL OUT BAD RATIOS
00778                          *
00779P 0513 34    14          A CULRAT PSHS    X,B
00780P 0515 F7    02A7        D        STB     CULNUM
00781P 0518 EC    04          A CULRA1 LDD     4,X         SLIDE RATIOS DOWN
00782P 051A ED    81          A        STD     ,X++
00783P 051C EC    04          A        LDD     4,X
00784P 051E ED    81          A        STD     ,X++
00785P 0520 7A    02A7        D        DEC     CULNUM
00786P 0523 26    F3    0518           BNE     CULRA1
00787P 0525 7A    02A9        D        DEC     NUMRAT+1
00788P 0528 35    14          A        PULS    X,B
00789P 052A 30    1C          A        LEAX    -4,X
00790P 052C 39                         RTS
00791
00793                          ****************************************************
00794                          *
00795                          *   PRINTER OUTPUT ROUTINE
00796                          *
00797                          ****************************************************
00798
00799P 052D B7    AF11        A POUCH  STA     PIA2BD      SEND CHAR TO PRINTER
00800P 0530 86    3E          A        LDA     #$3E        STROBE HIM
00801P 0532 B7    AF13        A        STA     PIA2BC
00802P 0535 B6    AF13        A PWAIT  LDA     PIA2BC      CHECK FLAG
00803P 0538 2A    FB    0535           BPL     PWAIT       WAIT TILL SET
00804P 053A 86    36          A        LDA     #$36        RESET STROBE
00805P 053C B7    AF13        A        STA     PIA2BC
00806P 053F B6    AF11        A        LDA     PIA2BD      DUMMY READ TO CLEAR FLAG
00807P 0542 39                  RTRN2  RTS                 RETURN
00808                          *
00809                          *   OUTPUT STRING TO PRINTER
00810                          *
00811P 0543 4F                  PDATA  CLRA
00812P 0544 8D    E7    052D           BSR     POUCH       'NOP'
00813P 0546 4F                         CLRA
00814P 0547 8D    E4    052D           BSR     POUCH       'NOP'
00815P 0549 A6    80          A        LDA     ,X+
00816P 054B 81    04          A        CMPA    #EOT
00817P 054D 27    F3    0542           BEQ     RTRN2       RETURN AT END OF STRING
00818P 054F 8D    DC    052D           BSR     POUCH
00819P 0551 20    F0    0543           BRA     PDATA
00820
00822                          *
00823                          *   PRINT ROUTINES
00824                          *
00825P 0553 8E    093A        P PRTNOR LDX     #NORFP
00826P 0556 8D    EB    0543           BSR     PDATA
00827P 0558 39                         RTS
00828P 0559 34    60          A PRTRES PSHS    U,Y
00829P 055B 8E    097A        P        LDX     #AROCLR
00830P 055E 8D    E3    0543           BSR     PDATA
00831P 0560 108E  004D        D        LDY     #RNAME
00832P 0564 8E    0009        D        LDX     #NUMBUF
00833P 0567 17    01C5  072F           LBSR    BTOASC
00834P 056A CC    0D04        A        LDD     #$0D04
00835P 056D ED    84          A        STD     ,X
00836P 056F 8E    0009        D        LDX     #NUMBUF
00837P 0572 8D    CF    0543           BSR     PDATA
00838P 0574 8E    0981        P        LDX     #AMATCH
00839P 0577 8D    CA    0543           BSR     PDATA
00840P 0579 8E    0009        D        LDX     #NUMBUF
00841P 057C 108E  004F        D        LDY     #RMATCH
00842P 0580 17    01AC  072F           LBSR    BTOASC
00843P 0583 CC    0D04        A        LDD     #$0D04
00844P 0586 ED    84          A        STD     ,X
00845P 0588 8E    0009        D        LDX     #NUMBUF
00846P 058B 8D    B6    0543           BSR     PDATA
00847P 058D 8E    0009        D        LDX     #NUMBUF
00848P 0590 108E  0051        D        LDY     #RMEAN
00849P 0594 17    0198  072F           LBSR    BTOASC
00850P 0597 CC    706D        A        LDD     #$706D      PPM
00851P 059A A7    80          A        STA     ,X+
00852P 059C ED    81          A        STD     ,X++
00853P 059E CC    202B        A        LDD     #$202B
00854P 05A1 ED    81          A        STD     ,X++
00855P 05A3 CC    2F2D        A        LDD     #$2F2D
00856P 05A6 ED    81          A        STD     ,X++
00857P 05A8 108E  0053        D        LDY     #RDIFF
00858P 05AC 17    0180  072F           LBSR    BTOASC
00859P 05AF CC    706D        A        LDD     #$706D      PPM
00860P 05B2 A7    80          A        STA     ,X+
00861P 05B4 ED    81          A        STD     ,X++
```

```
00862P 05B6 CC   0D0A       A         LDD    #$0D0A
00863P 05B9 ED   81         A         STD    ,X++
00864P 05BB 86   04         A         LDA    #$04
00865P 05BD A7   84         A         STA    ,X
00866P 05BF 8E   0009       D         LDX    #NUMBUF
00867P 05C2 17   FF7E 0543            LBSR   PDATA
00868P 05C5 35   60         A         PULS   U,Y
00869P 05C7 39                        RTS
00870                       *
00871P 05C8 7D   0023       D PRTCAL  TST    CALBRT
00872P 05CB 27   1C   05E9            BEQ    FRCREC        FORCE RECALIBRATION
00873P 05CD 8E   08A1       P         LDX    #WELCOM
00874P 05D0 17   FF70 0543            LBSR   PDATA
00875P 05D3 86   0A         A         LDA    #NCAL
00876P 05D5 B7   0025       D         STA    NUMSMP        NUMBER OF SAMPLES COUNTER
00877P 05D8 39                        RTS
00878                       *
00879P 05D9 8E   08DC       P PRTLOF  LDX    #LOFLOW
00880P 05DC 20   08   05E6            BRA    PRTREC
00881P 05DE 8E   08EC       P PRTSMP  LDX    #DIRTY
00882P 05E1 20   03   05E6            BRA    PRTREC
00883P 05E3 8E   0912       P PRTCNT  LDX    #CONTAM
00884P 05E6 17   FF5A 0543 PRTREC LBSR PDATA
00885P 05E9 7F   0025       D FRCREC  CLR    NUMSMP
00886P 05EC 7F   0023       D         CLR    CALBRT
00887P 05EF 39                        RTS
00888P 05F0 8E   094C       P PRTCOM  LDX    #COMPLX
00889P 05F3 17   FF4D 0543            LBSR   PDATA
00890P 05F6 39                        RTS
00891
00893                       ****************************************************************
00894                       *
00895                       *   SUBROUTINES USED IN SAMPLE OPERATIONS
00896                       *
00897                       ****************************************************************
00898
00899                       *
00900                       *   POLL THE PRINT SWITCH
00901                       *
00902P 05F7 86   40         A POLPRT  LDA    #SWPRNT
00903P 05F9 17   017B 0777            LBSR   CHKBIT        WAS THER A PRINT REQUEST?
00904P 05FC 27   03   0601            BEQ    POLPRX
00905P 05FE 17   00FC 06FD            LBSR   PRTTMP        PRINT THE TEMPS
00906P 0601 8D   01   0604  POLPRX    BSR    GETTMP        SETS 'Z' FLAG
00907P 0603 39                        RTS
00908
00909                       *   GET THE THERMOCOUPLE TEMPERATURES
00910                       *
00911P 0604 108E 0027       D GETTMP  LDY    #THERM1       -> THERMOCOUPLE DATA
00912P 0608 8E   AF40       A         LDX    #ADC          -> A-D
00913P 060B 4F                        CLRA                 CLEAR MSB
00914P 060C E6   01         A         LDB    1,X           PORT TEMP
00915P 060E ED   A4         A         STD    0,Y
00916P 0610 E6   02         A         LDB    2,X           COLUMN TEMP
00917P 0612 ED   22         A         STD    2,Y
00918P 0614 E6   03         A         LDB    3,X           DETECTOR TEMP
00919P 0616 ED   24         A         STD    4,Y
00920P 0618 8E   0083       A         LDX    #MAXTMP       NOW CHECK FOR TEMP OVERFLOW
00921P 061B AC   A4         A         CMPX   ,Y
00922P 061D 23   19   0638            BLS    GETTMO
00923P 061F AC   22         A         CMPX   2,Y
00924P 0621 23   15   0638            BLS    GETTMO
00925P 0623 AC   24         A         CMPX   4,Y
00926P 0625 23   11   0638            BLS    GETTMO
00927P 0627 8E   004F       A         LDX    #MINTMP       AND NOW CHECK FOR UNDERFLOW
00928P 062A AC   A4         A         CMPX   ,Y
00929P 062C 24   0D   063B            BHS    GETTMU
00930P 062E AC   22         A         CMPX   2,Y
00931P 0630 24   09   063B            BHS    GETTMU
00932P 0632 AC   24         A         CMPX   4,Y
00933P 0634 24   05   063B            BHS    GETTMU
00934P 0636 4F                        CLRA                 SET 'EQ'
00935P 0637 39                        RTS
00936P 0638 86   01         A GETTMO  LDA    #$01          SET 'GT'
00937P 063A 39                        RTS
00938P 063B 86   FF         A GETTMU  LDA    #$FF          SET 'LT'
00939P 063D 39                        RTS
00940                       *
00941                       *   SET UP DAC ZERO
00942                       *
00943P 063E 86   80         A SETDAC  LDA    #DACMSK       GET INITIAL DAC MASK
00944P 0640 B7   002D       D         STA    MASK
00945P 0643 8E   AF50       A         LDX    #DAC          ->DAC
00946P 0646 108E AF26       A         LDY    #TIME3D       ->TIMER #3
00947P 064A 86   FF         A         LDA    #$FF          TRY TO ZERO DAC
00948P 064C A7   84         A         STA    ,X
00949P 064E B7   002E       D         STA    DACVAL
```

```
00950P 0651 8D    34    0687            BSR   DACDEL
00951P 0653 B6    002E  D    SETDA1 LDA  DACVAL
00952P 0656 B8    002D  D           EORA MASK
00953P 0659 A7    84    A            STA  ,X        INVERT MASKED BIT
00954P 065B B7    002E  D            STA  DACVAL
00955P 065E 8D    27    0687         BSR  DACDEL
00956P 0660 EC    A4    A            LDD  ,Y
00957P 0662 1083  FF7F  A            CMPD #DACHI
00958P 0666 23    09    0671         BLS  SETDA2
00959P 0668 B6    002E  D            LDA  DACVAL
00960P 066B B8    002D  D            EORA MASK
00961P 066E B7    002E  D            STA  DACVAL    RE-INVERT MASKED BIT
00962P 0671 74    002D  D    SETDA2 LSR  MASK      SHIFT MASK-BIT DOWN
00963P 0674 26    DD    0653         BNE  SETDA1    LOOP IF NOT DONE
00964P 0676 8D    0F    0687         BSR  DACDEL
00965P 0678 B6    002E  D            LDA  DACVAL
00966P 067B 81    10    A            CMPA #DACMIN
00967P 067D 25    02    0681         BLO  SETDAE
00968P 067F 4F                       CLRA
00969P 0680 39                       RTS            'EQ' SET
00970                        *
00971P 0681 17    FF5F  05E3 SETDAE LBSR PRTCNT    FORCE RECALIBRATION
00972P 0684 86    01    A            LDA  #1
00973P 0686 39                       RTS            'NE' SET ON ERROR
00974                        *
00975                        *   DELAY FOR DAC
00976                        *
00977P 0687 34    10    A    DACDEL PSHS X
00978P 0689 8E    AF00  A            LDX  #PIA1AD   -> PIA-CA1 IS CLOCK
00979P 068C A6    84    A            LDA  ,X        DUMMY READ TO CLEAR
00980P 068E C6    08    A            LDB  #DACTIM   DAC SETTLING FACTOR
00981P 0690 6D    02    A    DACDE1 TST  2,X
00982P 0692 2A    FC    0690         BPL  DACDE1    LOOP TIL TIME-OUT
00983P 0694 A6    84    A            LDA  ,X        DUMMY READ
00984P 0696 C5    03    A            BITB #%00000011 FLASH MASK
00985P 0698 26    05    069F         BNE  DACDE2
00986P 069A 86    08    A            LDA  #LMPCAL
00987P 069C 17    00EB  078A         LBSR TGLBIT   FLASH CAL LAMP
00988P 069F 5A               DACDE2 DECB
00989P 06A0 26    EE    0690         BNE  DACDE1
00990P 06A2 35    10    A            PULS X
00991P 06A4 39                       RTS
00992                        *
00993                        *   GET A SAMPLE FROM ELECTROMETER
00994                        *
00995P 06A5 7D    AF02  A    GETSMP TST  PIA1AC
00996P 06A8 2A    FB    06A5         BPL  GETSMP    WAIT FOR 1/4 SECOND
00997P 06AA B6    AF00  A            LDA  PIA1AD    DUMMY READ TO CLEAR PIA
00998P 06AD FC    0021  D            LDD  ELPSDT
00999P 06B0 83    0001  A            SUBD #1
01000P 06B3 FD    0021  D            STD  ELPSDT    DECREMENT TIME
01001P 06B6 FC    AF21  A            LDD  TIMEST    DUMMY READ STATUS
01002P 06B9 FC    AF26  A            LDD  TIME3D
01003P 06BC 1083  FFFF  A            CMPD #$FFFF
01004P 06C0 27    02    06C4         BEQ  GETSMX
01005P 06C2 43                       COMA          INVERT COUNT
01006P 06C3 53                       COMB
01007P 06C4 39               GETSMX RTS
01008                        *
01009                        *   GET INITIAL SOLVENT PEAK (START OF SAMPLE)
01010                        *
01011P 06C5 CC    01E0  A    GETSOS LDD  #T2MIN    SET TIME-OUT
01012P 06C8 FD    0021  D            STD  ELPSDT
01013P 06CB 8D    D8    06A5         BSR  GETSMP
01014P 06CD FD    0040  D            STD  LSTVAL
01015P 06D0 FC    0021  D    GETSO1 LDD  ELPSDT
01016P 06D3 27    17    06EC         BEQ  GETSOX
01017P 06D5 8D    CE    06A5         BSR  GETSMP
01018P 06D7 1F    03    A            TFR  D,U
01019P 06D9 B3    0040  D            SUBD LSTVAL
01020P 06DC 2C    05    06E3         BGE  GETSO2
01021P 06DE 43                       COMA
01022P 06DF 53                       COMB
01023P 06E0 C3    0001  A            ADDD #1
01024P 06E3 FF    0040  D    GETSO2 STU  LSTVAL
01025P 06E6 1083  003C  A            CMPD #SOLTHR
01026P 06EA 2F    E4    06D0         BLE  GETSO1
01027P 06EC 39               GETSOX RTS            EQ=NO SOLVENT, NE=SOLVENT
01028                        *
01029                        *   CONVERT TEMPERATURES TO DEGREES C
01030                        *
01031P 06ED 8E    0027  D    CNVTMP LDX  #THERM1   POINT TO TEMPERATURES
01032P 06F0 EC    84    A    CNVTM1 LDD  ,X
01033P 06F2 C3    0095  A            ADDD #TMPOFF   OFFSET TEMP
01034P 06F5 ED    81    A            STD  ,X++
01035P 06F7 8C    002B  D            CMPX #THERM3
01036P 06FA 2F    F4    06F0         BLE  CNVTM1
01037P 06FC 39                       RTS
01038                        *
```

```
01039                   *   PRINT THE CURRENT TEMPERATURES
01040                   *
01041P 06FD 86   02    A PRTTMP LDA    #LMPPRT
01042P 06FF 8D   7A  077B      BSR    SETBIT    TURN ON THE PRINT LAMP
01043P 0701 8D   EA  06ED      BSR    CNVTMP    CONVERT THE TEMPERATURES
01044P 0703 8E   0852   P      LDX    #WATEMP
01045P 0706 17   FE3A 0543     LBSR   PDATA     PRINT HEADING
01046P 0709 108E 0027   D      LDY    #THERM1   POINT TO TEMPERATURES
01047P 070D 8E   0009   D      LDX    #NUMBUF
01048P 0710 CC   2020   A      LDD    #$2020
01049P 0713 ED   81     A      STD    ,X++
01050P 0715 8D   18  072F      BSR    BTOASC    CONVERT TEMP1 TO ASCII
01051P 0717 8D   16  072F      BSR    BTOASC    CONVERT TEMP2 TO ASCII
01052P 0719 8D   14  072F      BSR    BTOASC    CONVERT TEMP3 TO ASCII
01053P 071B CC   0D0A   A      LDD    #$0D0A    CR, LF
01054P 071E ED   81     A      STD    ,X++
01055P 0720 86   04     A      LDA    #$04      EOT
01056P 0722 A7   84     A      STA    ,X
01057P 0724 8E   0009   D      LDX    #NUMBUF
01058P 0727 17   FE19 0543     LBSR   PDATA
01059P 072A 86   02     A      LDA    #LMPPRT
01060P 072C 8D   54  0782      BSR    CLRBIT    TURN OFF PRINT LAMP
01061P 072E 39                 RTS
01062                   *
01063                   *   PRINT 16 BIT NUMERIC DATA
01064                   *
01065P 072F EC   A1     A BTOASC LDD   ,Y++      GET DATA
01066P 0731 34   20     A      PSHS   Y         SAVE Y
01067P 0733 108E 0000   D      LDY    #MREGOH   POINT TO MATH REGISTERS
01068P 0737 ED   26     A      STD    6,Y       SAVE NUMBER AS REMAINDER
01069P 0739 CE   076F   P      LDU    #BTATBL   POINT TO B->A TABLE
01070P 073C 5F                 CLRB
01071P 073D 34   04     A BTALOP PSHS  B         SAVE LEADING 0 FLAG
01072P 073F EC   26     A      LDD    6,Y       GET REMAINDER
01073P 0741 ED   22     A      STD    2,Y
01074P 0743 EC   C1     A      LDD    ,U++
01075P 0745 ED   24     A      STD    4,Y
01076P 0747 6F   A4     A      CLR    0,Y
01077P 0749 6F   21     A      CLR    1,Y
01078P 074B 8D   4D  079A      BSR    DIVIDE    NUM/TABLE VALUE
01079P 074D A6   23     A      LDA    3,Y       GET DIGIT
01080P 074F 35   04     A      PULS   B
01081P 0751 1083 0000   A      CMPD   #0
01082P 0755 26   04  075B      BNE    BTALP1    CHECK FOR LEADING 0
01083P 0757 86   20     A      LDA    #$20      IF SO, BLANK IT
01084P 0759 20   03  075E      BRA    BTALP2
01085P 075B 8B   30     A BTALP1 ADDA  #$30      MAKE IT ASCII
01086P 075D 5C                 INCB             KILL LEADING ZERO FLAG
01087P 075E A7   80     A BTALP2 STA   ,X+       SAVE IN NUMBUF
01088P 0760 1183 0777   P      CMPU   #BTATBE
01089P 0764 26   D7  073D      BNE    BTALOP
01090P 0766 A6   27     A      LDA    7,Y       GET LAST DIGIT
01091P 0768 8B   30     A      ADDA   #$30      ASCIIZE
01092P 076A A7   80     A      STA    ,X+
01093P 076C 35   20     A      PULS   Y
01094P 076E 39                 RTS
01095P 076F      2710   A BTATBL FDB   10000,1000,100,10
01096             0777  P BTATBE EQU   *
01097                   *
01098                   *   CHECK A BIT IN 'SWITCH' PIA
01099                   *
01100P 0777 B4   AF01  A CHKBIT ANDA   PIA1BD    IS IT ON?
01101P 077A 39                 RTS              RETURN (NE=IT'S ON, EQ=IT'S OFF)
01102                   *
01103                   *   SET A BIT IN 'LAMPS' PIA
01104                   *
01105P 077B BA   AF01  A SETBIT ORA    PIA1BD    ADD IN NEW BITS WITH 'A'
01106P 077E B7   AF01  A        STA    PIA1BD    PUT IT BACK
01107P 0781 39                 RTS              RETURN ('A' CLOBBERED)
01108                   *
01109                   *   CLEAR A BIT IN 'LAMP' PIA
01110                   *
01111P 0782 43                 CLRBIT COMA      COMPLIMENT BITS IN 'A'
01112P 0783 B4   AF01  A        ANDA   PIA1BD   AND WITH COMPLIMENT
01113P 0786 B7   AF01  A        STA    PIA1BD   PUT RESULT BACK
01114P 0789 39                 RTS              RETURN ('A' CLOBBERED)
01115                   *
01116                   *   TOGGLE BIT IN 'LAMP' PIA
01117                   *
01118P 078A B8   AF01  A TGLBIT EORA   PIA1BD    COMPLIMENT BITS IN 'A'
01119P 078D B7   AF01  A        STA    PIA1BD    INDICATED
01120P 0790 39                 RTS              RETURN ('A' CLOBBERED)
01121                   *
01122                   *   SHORT DELAY LOOP FOR SWITCH DEBOUNCE, ETC.
01123                   *
01124P 0791 5F                 DELAY  CLRB
01125P 0792 4F                 DELAY1 CLRA
01126P 0793 4A                 DELAY2 DECA
```

```
01127P 0794 26     FD   0793            BNE      DELAY2
01128P 0796 5A                          DECB
01129P 0797 26     F9   0792            BNE      DELAY1
01130P 0799 39                          RTS
01131
01133                        ********************************************************************
01134                        *
01135                        *    MATH ROUTINES DIVIDE AND MULTIPLY
01136                        *
01137                        ********************************************************************
01138
01139P 079A 86     20    A DIVIDE LDA   #32         SET COUNT
01140P 079C 34     02    A        PSHS  A           SAVE ON STACK
01141P 079E 5F                    CLRB              CLEAR REMAINDER
01142P 079F 4F                    CLRA
01143P 07A0 68     23    A        ASL   3,Y         SHIFT LSB
01144P 07A2 69     22    A        ROL   2,Y
01145P 07A4 69     21    A        ROL   1,Y
01146P 07A6 69     A4   A         ROL   0,Y
01147P 07A8 59            DIVLOP ROLB               CARRY->LSB REMAINDER
01148P 07A9 49                    ROLA
01149P 07AA A3     24    A        SUBD  4,Y         SUBTRACT DIVIDEND
01150P 07AC 24     02   07B0      BCC   DIVID1      OK IF NO CARRY
01151P 07AE E3     24    A        ADDD  4,Y         ELSE ADD IT BACK
01152P 07B0 69     23    A DIVID1 ROL   3,Y
01153P 07B2 69     22    A        ROL   2,Y
01154P 07B4 69     21    A        ROL   1,Y
01155P 07B6 69     A4   A         ROL   0,Y
01156P 07B8 6A     E4    A        DEC   0,S         DROP COUNT
01157P 07BA 26     EC   07A8      BNE   DIVLOP      LOOP BACK
01158P 07BC 32     61    A        LEAS  1,S         POP STACK
01159P 07BE 63     23    A        COM   3,Y
01160P 07C0 63     22    A        COM   2,Y         FIX RESULT
01161P 07C2 63     21    A        COM   1,Y
01162P 07C4 63     A4   A         COM   0,Y
01163P 07C6 ED     26    A        STD   6,Y         SAVE REMAINDER
01164P 07C8 39                    RTS
01165
01166                        *
01167                        *    ROUND THE RESULT OF A DIVIDE OPERATION
01168                        *
01169P 07C9 EC     24    A ROUND  LDD   4,Y         GET DIVISOR
01170P 07CB 47                    ASRA
01171P 07CC 56                    RORB              DIVIDE IT BY 2
01172P 07CD 10A3 26       A       CMPD  6,Y         COMPARE TO REMAINDER
01173P 07D0 24     0F   07E1      BHS   ROUND1      BRA IF REM<=DIVISOR/2
01174P 07D2 EC     22    A        LDD   2,Y
01175P 07D4 C3   0001    A        ADDD  #1          ELSE ROUND QUOTIENT UP
01176P 07D7 ED     22    A        STD   2,Y         PUT QUOTIENT BACK
01177P 07D9 24     06   07E1      BCC   ROUND1
01178P 07DB 6C     21    A        INC   1,Y
01179P 07DD 24     02   07E1      BCC   ROUND1
01180P 07DF 6C     A4    A        INC   ,Y
01181P 07E1 39            ROUND1 RTS                AND RETURN
01182
01183                        *
01184                        *    MULTIPLY TO 16 BIT INTEGERS
01185                        *
01186P 07E2 6F     A4    A MULT16 CLR   0,Y         CLEAR RESULT
01187P 07E4 6F     21    A        CLR   1,Y
01188P 07E6 A6     25    A        LDA   5,Y         GET FIRST BYTE
01189P 07E8 E6     27    A        LDB   7,Y
01190P 07EA 3D                    MUL               MULTIPLY THEM
01191P 07EB ED     22    A        STD   2,Y         SAVE PARTIAL RESULT
01192P 07ED A6     24    A        LDA   4,Y         GET HI BYTE
01193P 07EF E6     27    A        LDB   7,Y
01194P 07F1 3D                    MUL
01195P 07F2 E3     21    A        ADDD  1,Y         ADD IT IN
01196P 07F4 ED     21    A        STD   1,Y         SAVE THAT NOW
01197P 07F6 24     02   07FA      BCC   MUL16A      CHECK CARRY
01198P 07F8 6C     A4    A        INC   0,Y
01199P 07FA A6     25    A MUL16A LDA   5,Y         NEXT BYTE
01200P 07FC E6     26    A        LDB   6,Y
01201P 07FE 3D                    MUL
01202P 07FF E3     21    A        ADDD  1,Y         ADD IT IN
01203P 0801 ED     21    A        STD   1,Y         SAVE RESULT
01204P 0803 24     02   0807      BCC   MUL16B
01205P 0805 6C     A4    A        INC   0,Y
01206P 0807 A6     24    A MUL16B LDA   4,Y         FINALLY BOTH HI BYTES
01207P 0809 E6     26    A        LDB   6,Y
01208P 080B 3D                    MUL
01209P 080C E3     A4    A        ADDD  0,Y
01210P 080E ED     A4    A        STD   0,Y
01211P 0810 39                    RTS
01212
01214                        ********************************************************************
01215                        *
01216                        *    TEXT STRINGS
01217                        *
01218                        ********************************************************************
```

```
01219
01220                        *
01221
01222P 0811     2A      A XSTEMP FCC     '*EMERGENCY SHUTDOWN*'
01223P 0825     0D      A        FCB     CR
01224P 0826     2A      A        FCC     '********************'
01225P 083A     0D      A        FCB     CR
01226P 083B     54      A        FCC     'TEMP. LIMIT EXCEEDED'
01227P 084F     0D      A        FCB     CR,LF,EOT
01228                        *
01229P 0852     20      A WATEMP FCC     '   TEMPERATURES (C)'
01230P 0865     0D      A        FCB     CR
01231P 0866     20      A        FCC     '    INJ  COL   DET'
01232P 0877     0D      A        FCB     CR,EOT
01233                        *
01234P 0879     20      A MOVNON FCC     '   PCBA-101 ENABLED'
01235P 088B     0D      A        FCB     CR
01236P 088C     20      A        FCC     '   OVENS HEATING UP'
01237P 089E     0D      A        FCB     CR,LF,EOT
01238                        *
01239P 08A1     20      A WELCOM FCC     '    PCBA-101 READY'
01240P 08B3     0D      A        FCB     CR,EOT
01241                        *
01242P 08B5     43      A REQCAL FCC     'CALIBRATION REQUIRED'
01243P 08C9     0D      A        FCB     CR,LF,EOT
01244                        *
01245P 08CC     49      A INJECT FCC     'INJECT SAMPLE'
01246P 08D9     0D      A        FCB     CR,LF,EOT
01247                        *
01248P 08DC     20      A LOFLOW FCC     '   CHECK FLOW'
01249P 08EA     0D      A        FCB     CR,EOT
01250                        *
01251P 08EC     43      A DIRTY  FCC     'CAL STANDARD OR'
01252P 08FB     0D      A        FCB     CR
01253P 08FC     53      A        FCC     'SYRINGE CONTAMINATED'
01254P 0910     0D      A        FCB     CR,EOT
01255                        *
01256P 0912     53      A CONTAM FCC     'SYSTEM CONTAMINATED'
01257P 0925     0D      A        FCB     CR,EOT
01258                        *
01259P 0927     4E      A NOSOLV FCC     'NO INJ. DETECTED'
01260P 0937     0D      A        FCB     CR,LF,EOT
01261                        *
01262P 093A     4E      A NORFP  FCC     'NO PCB DETECTED'
01263P 0949     0D      A        FCB     CR,LF,EOT
01264                        *
01265P 094C     53      A COMPLX FCC     'SAMPLE TOO COMPLEX'
01266P 095E     0D      A        FCB     CR
01267P 095F     20      A        FCC     '  FOR AUTOMATED'
01268P 096D     0D      A        FCB     CR
01269P 096E     20      A        FCC     '  ANALYSIS'
01270P 0977     0D      A        FCB     CR,LF,EOT
01271                        *
01272P 097A     20      A AROCLR FCC     '  PCB :'
01273P 0980     04      A        FCB     EOT
01274                        *
01275P 0981     20      A AMATCH FCC     '  MATCH ='
01276P 0989     04      A        FCB     EOT
01277                        *
01278P 098A     48      A XSSMPL FCC     'HIGH CONCENTRATION'
01279P 099C     0D      A        FCB     CR
01280P 099D     20      A        FCC     ' 30 MINUTE DELAY TO'
01281P 09B0     0D      A        FCB     CR
01282P 09B1     20      A        FCC     ' CLEAN SYSTEM.'
01283P 09BF     0D      A        FCB     CR
01284P 09C0     20      A        FCC     ' DILUTE AND REINJECT'
01285P 09D4     0D      A        FCB     CR,LF,EOT
01286                        *
01287P 09D7     20      A MERROR FCC     ' ERROR: SEE MANUAL'
01288P 09E9     0D      A        FCB     CR,LF,EOT
01289
01290           09EC    P ENDPRG EQU     *        END PROGRAM
01291
01293
01294                        *
01295                        *   SET UP INTERRUPT VECTORS
01296                        *
01297A 0000                        ASCT
01298A FFF0                        ORG     $FFF0
01299A FFF0     00AD    P          FDB     DUMRTI   RESERVED VECTOR
01300A FFF2     00AD    P          FDB     DUMRTI
01301A FFF4     00AD    P          FDB     DUMRTI
01302A FFF6     00AD    P          FDB     DUMRTI
01303A FFF8     00AD    P          FDB     DUMRTI
01304A FFFA     00AD    P          FDB     DUMRTI
01305A FFFC     00AD    P          FDB     DUMRTI
01306A FFFE     0000    A          FDB     START    POINT TO PASCAL PROGRAM
01307
01308                        *
```

```
01309                    *   ALLOCATE RAM STORAGE
01310                    *
01311D 0000                  DSCT
01312
01313                    *
01314                    *   TWO 32 BIT MATH REGISTERS FOR MULTIPLY AND DIVIDE
01315                    *
01316D 0000    0002    A MREGOH RMB    2           MATH REGISTERS
01317D 0002    0002    A MREGOL RMB    2
01318D 0004    0002    A MREG1H RMB    2
01319D 0006    0002    A MREG1L RMB    2
01320D 0008    0001    A SIGN   RMB    1
01321                    *
01322D 0009    0018    A NUMBUF RMB    24          ASCII NUMBER BUFFER
01323          0021    D NUMBFE EQU    *           END OF BUFFER
01324                    *
01325                    *   ELAPSED TIME SOFTWARE COUNTER
01326                    *
01327D 0021    0002    A ELPSDT RMB    2           ELAPSED TIME SINCE SAMPLE START
01328                    *
01329                    *   CONTROL FLAGS
01330                    *
01331D 0023    0001    A CALBRT RMB    1           SYSTEM CALIBRATED FLAG
01332D 0024    0001    A CALRUN RMB    1           ARM/CALIBRATE FLAG
01333D 0025    0001    A NUMSMP RMB    1           NUMBER OF SAMPLES TO TAKE
01334                    *
01335                    *   THERMOCOUPLE DATA
01336                    *
01337D 0026    0001    A ERROR  RMB    1           TEMPERATURE OVERFLOW FALSE=0/TRUE=1
01338D 0027    0002    A THERM1 RMB    2           THERMOCOUPLE-1
01339D 0029    0002    A THERM2 RMB    2           THERMOCOUPLE-2
01340D 002B    0002    A THERM3 RMB    2           THERMOCOUPLE-3
01341                    *
01342                    *   BASELINE SUBTRACT DATA AND BUFFERS
01343                    *
01344D 002D    0001    A MASK   RMB    1
01345D 002E    0001    A DACVAL RMB    1
01346D 002F    0001    A MULTVF RMB    1
01347D 0030    0002    A DATPTR RMB    2
01348D 0032    0002    A PEKPTR RMB    2
01349D 0034    0002    A VALPTR RMB    2
01350D 0036    0002    A PREVAL RMB    2
01351D 0038    0002    A PREVTM RMB    2
01352D 003A    0002    A PEKVAL RMB    2
01353D 003C    0002    A PEKTIM RMB    2
01354D 003E    0002    A INTGRL RMB    2
01355D 0040    0002    A LSTVAL RMB    2
01356D 0042    0002    A INTMIN RMB    2
01357D 0044    0002    A LOWINT RMB    2
01358D 0046    0002    A SMPCNT RMB    2
01359D 0048    0002    A SMPTIM RMB    2
01360D 004A    0001    A SCLINT RMB    1
01361D 004B    0002    A SCALE  RMB    2
01362D 004D    0002    A RNAME  RMB    2
01363D 004F    0002    A RMATCH RMB    2
01364D 0051    0002    A RMEAN  RMB    2
01365D 0053    0002    A RDIFF  RMB    2
01366D 0055    0002    A NUNK   RMB    2
01367          0057    D RAWDAT EQU    *
01368D 0057    0032    A INTBUF RMB    INTLEN      INTEGRATION BUFFER MUST PRECEED RAWBUF
01369          0089    D INTBFE EQU    *
01370D 0089    0200    A RAWBUF RMB    BUFLEN      RAW DATA BUFFER MUST PRECEED SLPBUF
01371          0289    D RAWBFE EQU    *
01372D 0289    0018    A SLPBUF RMB    SLPLEN      SLOPE BUFFER MUST PRECEED SMOBUF
01373          02A1    D SLPBFE EQU    *
01374D 02A1    0006    A SMOBUF RMB    SMOLEN      SMOOTH BUFFER MUST FOLLOW SLPBUF
01375          02A7    D SMOBFE EQU    *
01376          006F    D INTMID EQU    INTBUF+INTLO2-1
01377D 02A7    0001    A CULNUM RMB    1
01378D 02A8    0002    A NUMRAT RMB    2
01379          02AA    D RATIOS EQU    *           FOR PASCAL
01380D 02AA    012C    A PEKBUF RMB    300         PEAK TIME/INTEGRAL BUFFER
01381D 03D6    0064    A VALBUF RMB    100
01382D 043A    12C0    A DATBUF RMB    T10MIN*2
01383          16FA    D DATBFE EQU    *
01384          16FA    D ENDRAM EQU    *
01385                    END
```

TOTAL ERRORS 00000--00000

```
 1:0  PROGRAM PCBLIB;
 2:0  ($I+,R+,C+)
 3:0
 4:1  const MSTAND = 4;
 5:2        MPEAKS = 20;
 6:2
 7:1  TYPE  AROCLOR = record
 8:2                    NAME      : integer;
 9:2                    NPEAKS    : integer;
10:2                    REFTIME   : integer;
11:2                    TOTALAREA : real;
12:2                    RRTIME    : array[1..20] of real;
13:2                    AREA      : array[1..20] of integer
14:2                  end;
15:2
16:1  var   NUNK     : integer external;
17:2        RAWDATA  : array[1..MPEAKS,1..2] of integer external;
18:2        STANDARD : array[1..MSTAND] of AROCLOR external;
19:2        RNAME    : integer external;
20:2        RMATCH   : integer external;
21:2        RMEAN    : integer external;
22:2        RDIFF    : integer external;
23:2        SCALE    : integer external;
24:2        ERROR    : boolean external;
25:2        CALBRT   : boolean external;
26:2        CALRUN   : boolean external;
27:2        FMEAN    : real;
28:2
29:1  procedure INITIALIZE; external;
30:1
31:1  procedure POLMONITOR; external;
32:1
33:1  procedure CHKRATIOS; external;
34:1
35:1  procedure PRTNORFP; external;
36:1
37:1  procedure PRTCOMPLEX; external;
38:1
39:1  procedure PRTRESULTS; external;
40:1
41:1  procedure PRTLOFLOW; external;
42:1
43:1  procedure PRISMPLDIRTY; external;
44:1
45:1  procedure PRTCALIBRATED; external;
46:1
47:1  procedure LIBSEARCH;
48:1
49:2  const WINDOW2 = 0.03;
50:3        LOMATCH = 0;
51:3
52:2  var   UNKNOWN    : AROCLOR;
53:3        BEST       : integer;
54:3        BESTTIME   : real;
55:3        LOFIT      : boolean;
56:3        WINDOW1    : real;
57:3
58:2  procedure SETUNKS;
59:2
60:3  var I,UAREA: integer;
61:3
62*3  begin (SETUNKS)
63*4    UNKNOWN.TOTALAREA := 0.0;
64*4    for I := 1 to NUNK do begin
65*6      UAREA := RAWDATA[I,2];
66*6      UNKNOWN.AREA[I] := UAREA;
67*6      UNKNOWN.TOTALAREA := UNKNOWN.TOTALAREA + sqr(UAREA*1.0)
68:5    end (for I)
69*3  end; (SETUNKS)
70:3
71:3
72:2  procedure CALRRT(TIME : real);
73:2
74:3  var I : integer;
75:3
76*3  begin (CALRRT)
77*4    for I := 1 to NUNK do
78*5      UNKNOWN.RRTIME[I] := RAWDATA[I,1] / TIME;
79*3  end; (CALRRT)
80:3
81:3
82:2  procedure FINDBEST;
83:2
84:3  var IS    : integer;
85:4      NSTD  : integer;
86:4      SREFT : real;
87:4      STAREA: real;
88:4
89:3  procedure FINDRFP;
90:3
```

```
 91: 4   var IU     : integer;
 92: 5       MATCH  : integer;
 93: 5       LIM    : real;
 94: 5       TOTAL  : real;
 95: 5       ULTOTAL: real;
 96: 5       TIME   : real;
 97: 5       PURITY : real;
 98: 5       FIT    : real;
 99: 5       TEMP   : real;
100: 5
101: 4   procedure UPDATETOTALS;
102: 4
103: 5   var J, K   : integer;
104: 6       INC    : integer;
105: 6       INCR   : integer;
106: 6       TESTR  : real;
107: 6       RRTS   : real;
108: 6       SAREA  : real;
109: 6       ALASTK : real;
110: 6       ALASTS : real;
111: 6       LIM    : real;
112: 6       TEMP1  : real;
113: 6       TEMP2  : real;
114: 6
115*5   begin {UPDATETOTALS}
116*6     INC := 0;
117*6     for J := 1 to NSTD do begin
118*8       TESTR := 10.0;
119*8       ALASTK := 0.0;
120*8       ALASTS := 0.0;
121*8       SAREA := STANDARD[IS].AREA[J];
122*8       RRTS := STANDARD[IS].RRTIME[J];
123*8       LIM := WINDOW2 * RRTS;
124*8       INCR := INC + 1;
125*8       for K := INCR to NUNK do begin
126*A         TEMP1 := abs(UNKNOWN.RRTIME[K] - RRTS);
127*A         if (TEMP1 <= LIM) and (TEMP1< TESTR) then begin
128*D           TESTR := TEMP1;
129*D           INC := K;
130*D           TEMP1 := UNKNOWN.AREA[K];
131*D           TEMP2 := sqr(TEMP1);
132*D           TOTAL := TOTAL + TEMP2 - ALASTK;
133*D           ALASTK := TEMP2;
134*D           TEMP2 := TEMP1 * SAREA;
135*D           ULTOTAL := ULTOTAL + TEMP2 - ALASTS;
136*D           ALASTS := TEMP2
137:C         end {if}
138:9       end {for K}
139:7     end {for J}
140*5   end; {UPDATETOTALS}
141:5
142*4   begin {FINDRFP}
143*5     LIM := WINDOW1 * SREFT;
144*5     for IU := 1 to NUNK do begin
145*7       TEMP := RAWDATA[IU,1];
146*7       if abs(TEMP-SREFT) <= LIM then begin
147*A         TIME := TEMP;
148*A         CALRRT(TIME);
149*A         TOTAL := 0.0;
150*A         ULTOTAL := 0.0;
151*A         UPDATETOTALS;
152*A         TEMP := sqr(ULTOTAL) / STAREA;
153*A         FIT := TEMP/UNKNOWN.TOTALAREA;
154*A         MATCH := ROUND(FIT * TEMP/TOTAL * 1000.0);
155*A         if MATCH > RMATCH then begin
156*D           LOFIT := false;
157*D           if FIT < 0.9 then
158*F             LOFIT := true;
159*D           RNAME := STANDARD[IS].NAME;
160*D           RMATCH := MATCH;
161*D           BESTTIME := TIME;
162*D           BEST := IS
163:C         end {if}
164:9       end {if}
165:6     end {for IU}
166*4   end; {FINDRFP}
167:4
168*3   begin {FINDBEST}
169*4     for IS := 1 to MSTAND do begin
170*6       NSTD := STANDARD[IS].NPEAKS;
171*6       SREFT := STANDARD[IS].REFTIME;
172*6       STAREA := STANDARD[IS].TOTALAREA;
173*6       FINDRFP;
174:5     end {for}
175*3   end; {FINDBEST}
176:3
177:3
```

```
178:2  procedure REPORT;
179:2
180:3  procedure CALCONCENTRATION;
181:3
182:4  var   NUMRAT : integer external;
183:5        RATIOS : array[1..MPEAKS] of real external;
184:5        J      : integer;
185:5        MEAN   : real;
186:5        DIFF   : real;
187:5        FACTOR : real;
188:5
189:4  procedure CALRATIOS;
190:4
191:5  var INC,INCR : integer;
192:6      CK, J, K : integer;
193:6      RRTS     : real;
194:6      SAREA    : real;
195:6      LIM      : real;
196:6      TESTR    : real;
197:6      TEMP     : real;
198:6
199*5  begin {CALRATIOS}
200*6    INC := 0;
201*6    CK := 0;
202*6    for J := 1 to STANDARD[BEST].NPEAKS do begin
203*8      TESTR := 10.0;
204*8      SAREA := STANDARD[BEST].AREA[J];
205*8      RRTS := STANDARD[BEST].RRTIME[J];
206*8      LIM := WINDOW2 * RRTS;
207*8      INCR := INC + 1;
208*8      for K := INCR to NUNK do begin
209*A        TEMP := abs(UNKNOWN.RRTIME[K] - RRTS);
210*A        if (TEMP <= LIM) and (TEMP < TESTR) then begin
211*D          TESTR := TEMP;
212*D          INC := K;
213*D          if CK = J then
214*F            NUMRAT := NUMRAT - 1;
215*D          CK := J;
216*D          NUMRAT := NUMRAT + 1;
217*D          RATIOS[NUMRAT] := UNKNOWN.AREA[K] / SAREA
218:C        end {if}
219:9      end {for K}
220:7    end {for J}
221*5  end; {CALRATIOS}
222:5
223:4  procedure CALIBRATE;
224:4
225:5  const TIMEWINDOW = 0.2;
226:5
227:5  var SRRT : real;
228:5
229*5  begin {CALIBRATE}
230*6    CALBRT := true;
231*6    SRRT := STANDARD[3].REFTIME;
232*6    if abs(SRRT-BESTTIME)/SRRT > TIMEWINDOW then
233*8      PRTLOFLOW;
234*6    if LOFIT then
235*8      PRTSMPLDIRTY;
236*6    PRTCALIBRATED
237*5  end; {CALIBRATE}
238:5
239*4  begin {CALCONCENTRATIONS}
240*5    CALRRT(BESTTIME);
241*5    NUMRAT := 0;
242*5    CALRATIOS;
243*5    CHKRATIOS;
244*5    if NUMRAT > 0 then begin
245*8      MEAN := 0.0;
246*8      for J := 1 to NUMRAT do
247*9        MEAN := MEAN + RATIOS[J];
248*8      MEAN := (MEAN / NUMRAT);
249*8      DIFF := 0.0;
250*8      for J := 1 to NUMRAT do
251*9        DIFF := DIFF + abs(MEAN - RATIOS[J]);
252*8      FACTOR := FMEAN * SCALE;
253*8      MEAN := FACTOR * MEAN;
254*8      DIFF := FACTOR * DIFF / NUMRAT;
255*8      RMEAN := ROUND(MEAN);
256*8      RDIFF := ROUND(DIFF);
257*8      if CALRUN then begin
258*B        FMEAN := 100.0 * FMEAN / MEAN;
259*B        CALIBRATE
260:A      end {if}
261:7    end else
262*7      BEST := 0
263*4  end; {CALCONCENTRATIONS}
264:4
265*3  begin {REPORT}
266*4    if BEST > 0 then
```

```
267*6      CALCONCENTRATION;
268*4      if BEST = 0 then
269*6        if UNKNOWN. TOTALAREA < STANDARD[2]. TOTALAREA*2. 0 then
270*8          PRTNORFP
271:7        else
272*8          PRTCOMPLEX;
273:8    ( else begin)
274*4      PRTRESULTS
275:4    ( end) (if)
276*3    end; (REPORT)
277:3
278:3
279*2    begin (LIBSEARCH)
280*3      SETUNKS;
281*3      BEST := 0;
282*3      RMATCH := LOMATCH;
283*3      WINDOW1 := 0. 2;
284*3      if CALRUN then begin
285*6        WINDOW1 := 1. 0;
286*6        FMEAN := 100. 0 (100 * 1 / SCALE of STANDARD DATA)
287:5      end;
288*3      IF NUNK > 4 THEN FINDBEST;
289*3      REPORT
290*2    end; (LIBSEARCH)
291:2
292*1    begin (PCBMON)
293*2      repeat
294*3        INITIALIZE;
295*3        while not ERROR do begin
296*5          POLMONITOR;
297*5          if not ERROR then LIBSEARCH
298:4        end (do)
299*2      until false
300*1    end. (PCBMON)
No Compilation Errors
```

1. Portable apparatus for field testing to determine the presence of polychlorinated biphenyls (PCBs) in a material which may contain an interfering component and PCBs, said apparatus comprising:

a gas chromatographic column for separating polychlorobiphenyl components and having an input for receiving a sample and an output for providing separated component peaks;

an electron capture detector connected to the output of said column, said detector providing an analog electrical output which varies with magnitude and retention time of component peaks;

an analog to digital converter connected to the detector to convert the output of said detector to a digital signal and provide an output indicative thereof, wherein the output of said converter constitutes sample data;

a microprocessor connected to the output of said converter, said microprocessor including a memory in which is located data regarding magnitudes and retention times for a plurality of standard PCB mixtures, said microprocessor further including means for comparing said sample data with the PCB standard data for recognition of a substantially similar elution pattern therewith and an output for indicating the presence of a PCB in a sample; and indication means responsive to the microprocessor output for providing indication of the presence of a PCB in a sample, said microprocessor further including means for determining with high certainty that a sample contains a PCB, for determining that a sample may contain a PCB and for determining with high certainty that a sample does not contain a PCB, said microprocessor further including means for causing said indication means to signal that a PCB is present in a sample, further testing of a sample should be undertaken, or no PCB is present in a sample, respectively.

2. Portable apparatus as set forth in claim 1 wherein said column, detector, converter, microprocessor and indication means are housed in a common enclosure.

3. Portable apparatus as set forth in claim 1 wherein said indication means is a printer.

4. Portable apparatus as set forth in claim 1 wherein said microprocessor comprises means for calculating the concentration of PCBs in a sample.

5. A method for field testing to determine the presence of polychlorinated biphenyls (PCBs) in a material which may contain an interfering component and PCBs, using automated test equipment including a gas chromatographic column, an electron capture detector and a microprocessor including a memory in which is located data regarding magnitudes and retention times for a plurality of standard PCB mixtures, said method comprising the following steps:

(a) preparing a sample by mixing a portion of said material with sulfuric acid for reacting with and retaining any interfering component, and with a lower alkane for partitioning off PCBs with said sample being a portion of said lower alkane and PCBs;

(b) separating polychlorobiphenyl components in said sample using said gas chromatographic column which has an input for receiving said sample and an output for providing separated component peaks;

(c) providing an electrical output signal including information regarding the magnitude and retention time of component peaks using said electron capture detector which is connected to the output of said column;

(d) comparing said electrical output with the contents of said memory through the use of said microprocessor; and (e) indicating one of the following: (1) the presence of a PCB in said sample based upon the comparison, (2) further testing of the sample should be undertaken or (3) no PCB is present in the sample.

* * * * *

UNITED STATES PATENT AND TRADEMARK OFFICE
CERTIFICATE OF CORRECTION

PATENT NO. : 4,944,921  Page 1 of 2
DATED : July 31, 1990
INVENTOR(S) : Bruce N. Colby et al.

It is certified that error appears in the above-identified patent and that said Letters Patent is hereby corrected as shown below:

On the title page, after "Filed: Mar. 6, 1984" insert -- Related Application Data: Continuation-in-part of International Application No. PCT/US83/00325, filed Mar. 7, 1983--.

Face of Patent, under U.S. Patent Documents, change the issue date of the "Solomon" reference from "3/1974" to --3/1976--.

Face of Patent, under U.S. Patent Documents, change the issue date of the "Kallos" reference from "9/1975" to --8/1977--.

Face of Patent, under U.S. Patent Documents, change the issue date of the "Bradshaw" reference from "9/1978" to --9/1979--.

Face of Patent, under U.S. Patent Documents change the issue date of the "Godsey" reference from "3/1975" to --3/1974--.

Face of Patent, under U.S. Patent Document change the issue date of the "Fletcher et al." reference from "3/1975" to --3/1974--.

Column 1, line 59, delete "of the".

UNITED STATES PATENT AND TRADEMARK OFFICE
CERTIFICATE OF CORRECTION

PATENT NO. : 4,944,921
DATED : July 31, 1990
INVENTOR(S) : Bruce N. Colby et al.

It is certified that error appears in the above-identified patent and that said Letters Patent is hereby corrected as shown below:

Column 4, line 30, change "electonegative" to --electronegative--.

Column 4, line 32, change "electonegative" to --electronegative--.

Column 4, line 56, change "Arocolor" to --Aroclor--.

Column 8, line 9, change "preceeding" to --preceding--.

Column 8, line 21, change "preceeding" to --preceding--.

Column 10, line 43, change "can not" to --cannot--.

Column 12, line 23, move "What Is Claimed Is:" to Column 49, line 26.

Signed and Sealed this

Twenty-first Day of April, 1992

Attest:

HARRY F. MANBECK, JR.

Attesting Officer

Commissioner of Patents and Trademarks